(12) United States Patent
Chan et al.

(10) Patent No.: US 8,962,808 B2
(45) Date of Patent: Feb. 24, 2015

(54) EGFR-RELATED POLYPEPTIDES AND METHODS OF USE

(75) Inventors: Edward L. Chan, Mt. Sinai, NY (US); James Keller, Islip, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 13/696,291

(22) PCT Filed: May 5, 2011

(86) PCT No.: PCT/US2011/035421
§ 371 (c)(1),
(2), (4) Date: Mar. 25, 2013

(87) PCT Pub. No.: WO2011/140391
PCT Pub. Date: Nov. 10, 2011

(65) Prior Publication Data
US 2013/0210004 A1   Aug. 15, 2013

Related U.S. Application Data

(60) Provisional application No. 61/331,815, filed on May 5, 2010.

(51) Int. Cl.
| | | |
|---|---|---|
| *C07K 16/00* | (2006.01) | |
| *C12Q 1/68* | (2006.01) | |
| *C07K 14/71* | (2006.01) | |
| *G01N 33/574* | (2006.01) | |
| *C07K 16/40* | (2006.01) | |
| *C12N 9/12* | (2006.01) | |
| *G01N 33/74* | (2006.01) | |

(52) U.S. Cl.
CPC ............. *C12Q 1/6886* (2013.01); *C07K 14/71* (2013.01); *G01N 33/57407* (2013.01); *C07K 16/40* (2013.01); *C12N 9/12* (2013.01); *G01N 33/74* (2013.01); *C07K 2319/00* (2013.01); *C07K 2319/23* (2013.01); *C07K 2319/42* (2013.01); *C07K 2319/43* (2013.01); *C07K 2319/60* (2013.01); *G01N 2333/71* (2013.01); *G01N 2800/56* (2013.01)
USPC .................. 530/388.22; 530/387.1; 530/387.9

(58) Field of Classification Search
None
See application file for complete search history.

(56) References Cited

U.S. PATENT DOCUMENTS

2007/0083334 A1*   4/2007   Mintz et al. ..................... 702/19

OTHER PUBLICATIONS

Sok et al. (2006) Clin. Cancer Res. 12: 5064-5073.*

* cited by examiner

*Primary Examiner* — Michael Pak
(74) *Attorney, Agent, or Firm* — Occhiuti & Rohlicek LLP

(57) ABSTRACT

Described herein are truncated EGF receptor polypeptides, nucleic acids encoding them, and methods of using them to help select a method of treatment for an EGFR-related cancer, to predict clinical outcome, and to detect micrometastases or minimal residual disease. High EGFR expression and phosphorylated EGFR predicts poor survival in head and neck cancer patients, but does not correlate with advanced stage disease. In our studies, we determined that clinical biological correlates are likely to be more accurate when different aspects of EGFR are evaluated in combination. We analyzed EGFR phosphorylation, expression and mutations in 60 primary head and neck tumors. We not only found that head and neck tumors with either truncated or activated EGFR tend to have higher tumor and nodal stage, but also discovered three EGFR truncations.

4 Claims, 14 Drawing Sheets

```
atgcgaccctccggggacggccggggcagcgctcctgccgctgctgctggctgcgctctgccggcgagtcggctc
tggaggaaagaaagTTTGCCAAGGCACGAGTAACAAGCTCACGCAGTTGGGCA
CTTTGAAGATCATTTCTCAGCCTCCAGAGGATGTTCAATAACTGTGAGGT
GGTCCTTGGGAATTTGGAAATTACCTATGTGCAGAGGAATTATGATCTTTCC
TTCTTAAAGaccatccagaggagtggctggttatgtcctcattgccctcaacacagtggacgaattccttgg
aaaacctgcagatcatcagagaggaaatatgtactacgaaaattccatgcctagcagttcttatctaactatgatgc
aaataaaaccgactgaaggagctgcccatgaagaaatttacaggAAATCCTGCATGGCGCGT
GCGGTTCAGCAACAACCCTGCCCTGTGCAACGTGGAGAGCATCCAGTGGC
GGGACATAGTCAGCAGTGACTTTCTCAGCAACATGTCGATGGACTTCCAGA
ACCACCTGGGCAGCTGCcaaaagtgatccaagtgtccaatgggagctgctggggtgcagga
gaggaactgcagaaacTGACCAAATCATCTGTGCCCAGCAGTGCTCCGGGC
GCTGCCGTGGCAAGTCCCCCGGGAGACGCTGACTGCTGCCACAACCAGTGTGCTGCA
GGCTGCACAGGCCCCCGGGAGAGCGACTGCCTGgtctgccgcaaattccgagacgaa
gccacgtgcaaggacaccctgccccactcatgctctacaaccaccgtaccagatgatgaaccc
gagggcaaatacagctttggtgccacctgcgtgaagaagtgtcccGTAATTATGTGGTGACAGA
TCACGGCTCGTGCGTCCGAGCCTGTGGGGCCGTGTGGGGCCGACAGCTATGAGATGGAGG
AAGACGGGCGTCCGCAAGTGTAAGAAGTGCGAAGGGCCTTGCCGCAAAG
```

Table I. Clinical and pathological characteristics of patient population

| Characterisitics | No. of patients (%) |
|---|---|
| Sex | |
| Male | 45 (75%) |
| Female | 15 (25%) |
| Race | |
| White | 53 (88.3%) |
| Black | 2 (3.3%) |
| Asian | 1 (1.7%) |
| Unknown | 4 (6.7%) |
| Age | |
| <65 | 43 (71.7%) |
| ≥65 | 17 (28.3%) |
| Smoking | |
| Yes | 37 (61.7%) |
| No | 11 (18.3%) |
| Unknown | 12 (20%) |
| Alcohol | |
| Yes | 34 (56.7%) |
| No | 12 (20%) |
| Unknown | 14 (23.3%) |

| Characterisitics | No. of patients (%) |
|---|---|
| Tumor site | |
| Oropharynx | 41 (68.3%) |
| Larynx | 19 (31.7%) |
| T stage | |
| Tis/T1/T2 | 26 (43.3%) |
| T3/T4 | 33 (55%) |
| Tx | 1 (1.7%) |
| N stage | |
| N0/N1 | 27 (45%) |
| N2 | 27 (45%) |
| Nx | 6 (10%) |
| Differentiation | |
| Well | 10 (16.7%) |
| Moderate | 42 (70%) |
| Poor | 5 (8.3%) |
| Unknown | 3 (5%) |
| Perineural Invasion | |
| Yes | 25 (41.7%) |
| No | 15 (25%) |
| Unknown | 20 (33.3%) |
| Lymphovascular Invasion | |
| Yes | 18 (30%) |
| No | 35 (58.3%) |
| Unknown | 7 (11.7%) |

Figure 5

Table II. Correlation of disease stage and aspect of EGFR alone or in combination

|  | pEGFR | | | ΔEGFR | | | EGFR expression | | | p- or Δ EGFR | | |
|---|---|---|---|---|---|---|---|---|---|---|---|---|
|  | + | - | p | + | - | p | HIGH | LOW | p | + | - | p |
| T stage |  |  |  |  |  |  |  |  |  |  |  |  |
| Tis/1/2 | 11 | 15 | NS | 3 | 23 | 0.02 | 14 | 12 | NS | 11 | 15 | 0.02 |
| T3/4 | 13 | 20 |  | 13 | 20 |  | 22 | 11 |  | 24 | 9 |  |
| N stage |  |  |  |  |  |  |  |  |  |  |  |  |
| N0/1 | 8 | 19 | 0.16 | 6 | 21 | 0.14 | 16 | 11 | NS | 13 | 14 | 0.05 |
| N2 | 13 | 14 |  | 11 | 16 |  | 18 | 9 |  | 20 | 7 |  |
| Staging |  |  |  |  |  |  |  |  |  |  |  |  |
| 1/2 | 4 | 6 | NS | 0 | 10 | 0.0007 | 5 | 5 | NS | 4 | 6 | 0.13 |
| 3/4 | 17 | 27 |  | 27 | 17 |  | 29 | 15 |  | 29 | 15 |  | pEGFR: phosphorylated EGFR; ΔEGFR: truncated EGFR (i.e. EGFRvIII, EGFR Δ471 or EGFR Δ660); p- or ΔEGFR: phosphorylated or truncated EGFR; p: p-value (2-tailed); NS: not significant, p>0.3

Figure 6A
Figure 6B
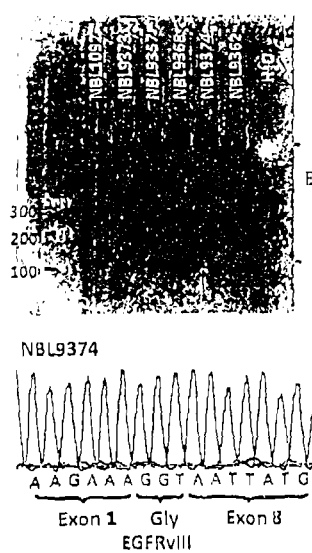
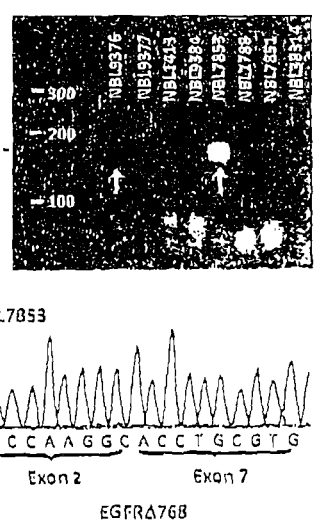
Figure 6C
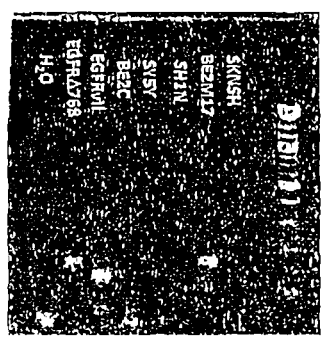

Figure 7B
Figure 7A
Figure 7D
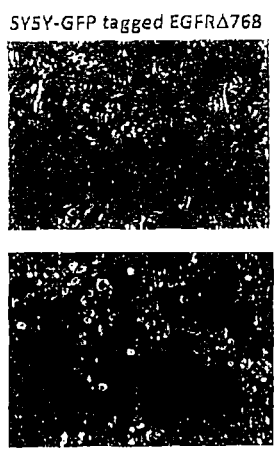
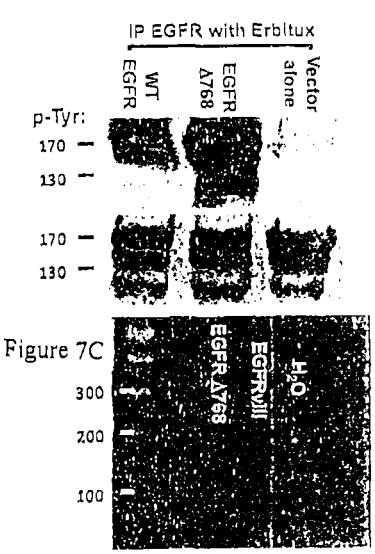
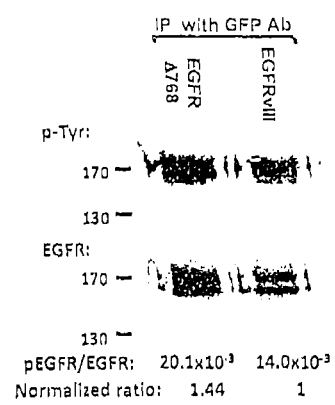
Figure 7E
Figure 7C

FIG. 10

```
MRPSGTAGAALLALLAALCPASRALEEKKvccgtcvkkcpRNYVVTDHGS      50
CVRACGADSYEMEEDGVRKCKKCEGPCRKVCNGIGIGEFKDSLSINATNI      100
KHFKNCTSISGDLHILPVAFRGDSFTHTPPLDPQELDILKTVKEITGFLL      150
IQAWPENRTDLHAFENLEIIRGRTKQHGQFSLAVVSLNITSLGLRSLKEI      200
SDGDVIISGNKNLCYANTINWKKLFGTSGQKTKIISNRGENSCKATGQVC      250
HALCSPEGCWGPEPRDCVSCRNVSRGRECVDKCNLLEGEPREFVENSECI      300
QCHPECLPQAMNITCTGRGPDNCIQCAHYIDGPHCVKTCPAGVMGENNTL      350
VWKYADAGhvchlchpnctygctgpglegcptngpkipsiatgmvgalll      400
Llvvalgiglfmrrhivrkrtlrrllqerelveplt psgeapnqallri      450
LKETEFKKIVLGSGAFGTVYKGLWIPEGEKVKIPVAIKELREATSPKAN      500
KEILDEAYVMASVDNPHVCRLLGICLTSTVQLITQLMPFGCLLDYVREHK      550
DNIGSQYLLNWCVQIAKGMNYLEDRRLVHRDLAARNVLVKTPQHVKITDF      600
GLAKLLGAEEKEYHAEGGKVPIKWMALESILHRIYTHQSDVWSYGVTVWE      650
LMTFGSKPYDGIPASEISSILEKGERLPQPPICTIDVYMIMVKCWMIDAD      700
SRPKFRELIIEFSKMARDPQRYLVIQGDERMHLPSPTDSNFYRALMDEED      750
MDDVVDADEYLIPQQGFSSPSTSRTPLLSSLSATSNNSTVACIDRNGLQ      800
SCPIKEDSFLQRYSSDPTGALTEDSIDDTFLPVPEYINQSVPKRPAGSVQ      850
NPVYHNQPLNPAPSRDPHYQDPHSTAVGNPEYLNTVQPTCVNSTFDSPAH     900
WAQKGSHQISLDNPDYQQDFFPKEAKPNGIFKGSTAENAEYLRVAPQSSE     950
FIGA 954
```

FIG. 11

```
          10         20         30         40         50
MRPSGTAGAALLALLAALCPASRALEekkgqkCDPSCPNGSCWGAGEENC          50
QKLTKIICAQQCSGRCRGKSPSDCCHNQCAAGCTGPRESDCLVCRKFRDE         100
ATCKDTCPPLMLYNPTTYQMDVNPEGKYSFGATCVKKCPRNYVVTDHGSC         150
VRACGADSYEMEEDGVRKCKKCEGPCRKVCNGIGIGEFKDSLSINATNIK         200
HFKNCTSISGDLHILPVAFRGDSFTHTPPLDPQELDILKTVKEITGFLLI         250
QAWPENRTDLHAFENLEIIRGRTKQHGQFSLAVVSLNITSLGLRSLKEIS         300
DGDVIISGNKNLCYANTINWKKLFGTSGQKTKIISNRGENSCKATGQVCH         350
ALCSPEGCWGPEPRDCVSCRNVSRGRECVDKCNLLEGEPREFVENSECIQ         400
CHPECLPQAMNITCTGRGPDNCIQCAHYIDGPHCVKTCPAGVMGENNTLV         450
WKYADAGHVCHLCHPNCTYGCTGPGLEGCPTNGPKIPSIATGMVGALLLL         500
LVVALGIGLFMRRRHIVRKRTLRRLLQERELVEPLTPSGEAPNQALLRIL         550
KETEFKKIKVLGSGAFGTVYKGLWIPEGEKVKIPVAIKELREATSPKANK         600
EILDEAYVMASVDNPHVCRLLGICLTSTVQLITQLMPFGCLLDYVREHKD         650
NIGSQYLLNWCVQIAKGMNYLEDRRLVHRDLAARNVLVKTPQHVKITDFG         700
LAKLLGAEEKEYHAEGGKVPIKWMALESILHRIYTHQSDVWSYGVTVWEL         750
MTFGSKPYDGIPASEISSILEKGERLPQPPICTIDVYMIMVKCWMIDADS         800
RPKFRELIIEFSKMARDPQRYLVIQGDERMHLSPTDSNFYRALMDEEDM         850
DDVVDADEYLIPQQGFFSSPSTSRTPLLSSLSATSNNSTVACIDRNGLQS         900
CPIKEDSFLQRYSSDPTGALTEDSIDDTFLPVPEYINQSVPKRPAGSVQN         950
PVYHNQPLNPAPSRDPHYQDPHSTAVGNPEYLNTVQPTCVNSTFDSPAHW        1000
AQKGSHQISLDNPDYQQDFFPKEAKPNGIFKGSTAENAEYLRVAPQSSEF        1050
IGA. 1054
```

Fig. 12

```
           10         20         30         40         50         60
MRPSGTAGAALLALLAALCPASRALEEKKVCQGTSNKLTQLGTFEDHFLSLQRMFNNCEV  60
VLGNLEITYVQRNYDlsffvvtDHGSCVRACGADSYEMEEDGVRKCKKCEGPCRKVCNGI 120
GIGEFKDSLSINATNIKHFKNCTSISGDLHILPVAFRGDSFTHTPPLDPQELDILKTVKE 180
ITGFLLIQAWPENRTDLHAFENLEIIRGRTKQHGQFSLAVVSLNITSLGLRSLKEISDGD 240
VIISGNKNLCYANTINWKKLFGTSGQKTKIISNRGENSCKATGQVCHALCSPEGCWGPEP 300
RDCVSCRNVSRGRECVDKCNLLEGEPREFVENSECIQCHPECLPQAMNITCTGRGPDNCI 360
QCAHYIDGPHCVKTCPAGVMGENNTLVWKYADAGHVCHLCHPNCTYGCTGPGLEGCPTNG 420
PKIPSIATGMVGALLLLLVVALGIGLFMRRRHIVRKRTLRRLLQERELVEPLTPSGEAPN 480
QALLRILKETEFKKIKVLGSGAFGTVYKGLWIPEGEKVKIPVAIKELREATSPKANKEIL 540
DEAYVMASVDNPHVCRLLGICLTSTVQLITQLMPFGCLLDYVREHKDNIGSQYLLNWCVQ 600
IAKGMNYLEDRRLVHRDLAARNVLVKTPQHVKITDFGLAKLLGAEEKEYHAEGGKVPIKW 660
MALESILHRIYTHQSDVWSYGVTVWELMTFGSKPYDGIPASEISSILEKGERLPQPPICT 720
IDVYMIMVKCWMIDADSRPKFRELIIEFSKMARDPQRYLVIQGDERMHLPSPTDSNFYRA 780
LMDEEDMDDVVDADEYLIPQQGFFSSPSTSRTPLLSSLSATSNNSTVACIDRNGLQSCPI 840
KEDSFLQRYSSDPTGALTEDSIDDTFLPVPEYINQSVPKRPAGSVQNPVYHNQPLNPAPS 900
RDPHYQDPHSTAVGNPEYLNTVQPTCVNSTFDSPAHWAQKGSHQISLDNPDYQQDFFPKE 960
AKPNGIFKGSTAENAEYLRVAPQSSEFIGA.                              991
```

EGFR-RELATED POLYPEPTIDES AND METHODS OF USE

CROSS-REFERENCE TO RELATED APPLICATIONS

This application claims the benefit of the filing date of U.S. Provisional Application No. 61/331,815, which was filed on May 5, 2010. For the purpose of any U.S. application or patent that claims the benefit of U.S. Provisional Application No. 61/331,815, the content of that earlier filed application is hereby incorporated by reference in its entirety.

GOVERNMENT SUPPORT

This invention was made with government support awarded by the National Institutes of Health under grant number 1R21CA133652-01A2. The government has certain rights in the invention.

SEQUENCE LISTING

The present application contains a Sequence Listing that has been submitted in ASCII format via EFS-Web and is hereby incorporated by reference into the present specification in its entirety.

TECHNICAL FIELD

This invention relates to the discovery of new forms of the epidermal growth factor receptor (EGFR), which we expect to be useful in staging certain cancers, in screening patients to determine their susceptibility to treatment with EGFR inhibitors, and in identifying new chemotherapeutic agents.

BACKGROUND

Aberrant expression and/or signaling of some tyrosine kinase receptors have been recognized as important in carcinogenesis (Kolibaba and Druker, Biochim. Biophys. Acta. 1333:F217-248, 1997). To determine if a particular tyrosine kinase receptor carries prognostic value, many translational studies have used immunohistochemistry (IHC) to detect expression of the receptor in tumor specimens. While conventional IHC approaches are relatively easy to perform on materials that are readily available, they evaluate only one aspect of the receptor. When IHC was used to examine the expression of the epidermal growth factor receptor (EGFR) in head and neck squamous cell carcinomas (HNSCC), a strong association was noted between high EGFR expression and poor survival (Grandis et al., J. Natl. Cancer Inst. 90:824-832, 1998). However, EGFR staining was not predictive of advanced stage disease. Subsequent studies used either fluorescence resonance energy transfer (FRET) or phospho-specific IHC to measure EGFR phosphorylation in HNSCC. While there was a significant association between activated EGFR and disease-free survival, no correlation was found between phosphorylation and disease stage (Kong et al., Cancer. Res. 66:2834-2843, 2006; Hiraishi et al., Pathol. Oncol. Res. 12:87-91, 2006). In spite of the critical role of EGFR in HNSCC, its expression and phosphorylation are not the only determinants of aggressive disease. A recent study reported that 42% of HNSCC expressed the EGFR truncation mutant, EGFRvIII, where it contributes to enhanced growth and resistance to EGFR targeting by Erbitux® (Sok et al., Clin. Cancer Res. 12:5064-5073, 2006). Thus, the expression of EGFR variants may be another important aspect related to the role of EGFR in HNSCC. Few studies have examined EGFR status in primary pediatric tumors. Despite the readily detectable EGFR expression in primary neuroblastoma and a documented effect of gefitinib on different NBL cell lines, only certain patients have benefited from reversible EGFR inhibitors in clinical trials. There is a continuing need for diagnostic methods that allow more effective targeted therapies in cancer.

SUMMARY

On evaluation of EGFR status in primary head and neck squamous cell carcinomas (HNSCCs) and neuroblastoma, we discovered the expression of three EGFR truncations in these tumors. All of the truncated polypeptides contain in-frame deletions of the EGFR extracellular domain. They are termed EGFRΔ768 (which we may abbreviate to Δ768 or EGFR768), EGFRΔ660 (which we may abbreviate to Δ660 or EGFR660), and EGFRΔ471 (which we may abbreviate as Δ471 or EGFR471). Based on the tissue analyzed to date, EGFR768 is predominantly expressed in neuroblastoma, while EGFR471 and EGFR660 were found in HNSCCs. EGFR768 carries an in-frame deletion from nucleotide 102 of exon 2 to nucleotide 869 of exon 7. This truncation results in a transcript with sequences coding for 11 more amino acids than EGFRvIII. About 15% of primary neuroblastoma express this variant. In addition, we found that one of five neuroblastoma cell lines naturally express this same variant. On the other hand, we found that close to 35% of head and neck tumors expressed the EGFR471 and EGFR660 variants. EGFR471 has an in-frame deletion from nucleotide 89 of exon 1 to nucleotide 559 of exon 4 with the formation of a new codon (GGC) in the splice junction. This translates to a glycine residue, similar to that seen in EGFRvIII. The second truncated variant, EGFR660 has an in-frame deletion from nucleotide 237 of exon 2 to nucleotide 896 of exon 8. Again, there is the formation of a new codon (TTT) at the splice junction, which translates into a phenylalanine residue. We also found that advanced stage head and neck tumors express either of these variants. To our knowledge, none of these variants has been reported or found in primary human tumors or cell lines. All of the truncations involve a portion of the extracellular domain, leaving the intrinsic tyrosine kinase activity intact. It is our belief that these variants possess oncogenic potential, just like EGFRvIII. Further, we postulate that the mutants render EGFR expressing tumors resistant to certain EGFR inhibitors such as the monoclonal antibodies developed to treat EGFR-associated cancers (e.g., ERBITUX). Thus, these mutants are useful as biomarkers for predicting patients' responses to EGFR targeting agents. Given their oncogenic potential, the truncation mutants described herein can also be used as therapeutic targets for drug and antibody development. Finally, the selective expression of the mutants makes them useful in molecular diagnostic methods. For example, detecting expression of the mutants (e.g., by PCR) can serve to detect micrometastasis or minimal residual disease (MRD) (e.g., in serum or bone marrow).

Accordingly, and more specifically, the present invention features polypeptides that include or consist of the amino acid sequences described herein as EGFR768; polypeptides comprising or consisting of the amino acid sequences described herein as EGFR660; and polypeptides comprising or consisting of the amino acid sequences described herein as EGFR471. As described further below, the polypeptides can be isolated or substantially purified from the in vivo environment in which they are naturally found. Also featured are polypeptides that are at least or about 70% (e.g., at least or about 70%, 75%, 80%, 85%, 90%, 95%, or 98%) identical to the sequences of EGFR768, EGFR660, EGFR471, or a portion thereof (e.g., the extracellular domain). Polypeptides exhibiting a certain degree of identity to the present polypeptides may represent truncated EGFRs from other species, and the invention encompasses polypeptides (e.g., EGFR768, EGFR660, and EGFR471) that are of mammalian origin (e.g., of rodent, rabbit, bovine, porcine, canine, feline, equine, goat, or sheep origin). Preferred polypeptides are of human origin. The polypeptides can include an EGFR sequence as described herein and a heterologous polypeptide in the form of a fusion protein or protein conjugate. The heterologous polypeptide may serve to increase the circulating half-life of the EGFR polypeptide, to increase its immunogenicity, or as a marker or tag. Wild type EGFR and at least one other truncation mutant, EGFRvIII, were known at the time the present application was filed; the polypeptides of the present invention therefore exclude these polypeptides.

Also within the scope of the present invention are isolated nucleic acids encoding one or more of the polypeptides of the present invention and expression vectors (e.g., plasmid or viral vectors) ecoding one or more of these polypeptides. Host cells that harbor or include the expression vectors, and which can therefore be used to express a polypeptide of the present invention, are also encompassed. Many types of cells suitable as host cells, including eukaryotic (e.g., human) and procaryotic cells are known in the art.

One or more of the polypeptides just described (e.g., EGFR471, EGFR660, EGFR768, any combination thereof, and/or related polypeptides, including fusion proteins or conjugates including these polypeptides and polypeptides that exhibit a high degree of identity there, particularly in the extracellular domains) can be packaged with instructions for use into a kit. Similarly, an agent that specifically binds one or these polypeptides (e.g., an antibody or other target-specific polypeptide) or an agent that specifically amplifies or detects a gene or mRNA encoding one or more of the polypeptides can be packaged into a kit with instructions for detecting the polypeptide, gene, or mRNA in a sample obtained from a patient (e.g., a patient having or suspected of having an EGFR-associated cancer such as a head and neck cancer (e.g., HNSCC) or a neuroblastoma). The significance of the expression detected is described further below. We note here that the present compositions can be used in methods of detecting cancer as well as assessing the stage of a cancer associated with EGFR mis-expression. The methods can include the steps of assessing both the degree of phosphorylation of EGFR expressed by cells within the cancer (e.g., in a sample, such as a biopsy sample, obtained from the patient) and the presence and/or nature (e.g., the type or extent) of any truncation of the EGFR in cells within the cancer. The combination of phosphorylated and truncated EGFR correlates with an advanced stage of the cancer (e.g., advanced tumor and nodal stage). As our studies indicate that these two aspects of EGFR expression may predict a patients' response to EGFR targeting therapy, the invention further features methods of assessing these aspects of EGFR expression in order to assess the likelihood that a patient will respond positively to a given chemotherapy (e.g., an EGFR-binding compound or antibody). It is our expectation that patients with tumors carrying activated EGFR will respond better to such chemotherapeutics (e.g., Erbitux®) than those with a truncated EGFR. When analyzed in combination, we believe truncated EGFR synergizes with phosphorylated EGFR in the correlation with advanced stage disease. HNSCC with either truncated forms of EGFR or activated full length EGFR tend to be of higher tumor and nodal stage. Thus, activated and truncated EGFR together represent biomarkers for aggressive HNSCC, and methods of analyzing receptor activation and length therefore provide a way to stage at least this type of cancer.

Among the methods of the present invention are methods of immunizing a mammal to elicit an immune response, including the production of antibodies, to a polypeptide described herein (e.g., EGFR471 or EGFR660). The antibodies may then be used as diagnostic and therapeutic agents. The mammal can be a mouse, rabbit, goat, or rat, and the polypeptide immunogen can be administered subcutaneously, intradermally, intravenously, or intraperitoneally.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 3 shows the sequence of exons 1-8 of the wild type EGFR (SEQ ID NO: 19). Successive exons are demarked by a change from lower case to upper case lettering.

FIG. 4 shows Table 1, which summarizes clinical and pathological characteristics of the patient population.

FIG. 5 shows Table 2, which summarizes correlation of disease state and aspect of EGFR alone of in combination.

FIGS. 6A and 6B show the results of an RT-PCR analysis of a panel of neuroblastoma tumors that express EGFR truncation mutants and the DNA sequencing results for NBL9374 (SEQ ID NO: 20)and NBL7853(SEQ ID NO: 13). FIG. 6C shows the results of an RT-PCR analysis of EGFR truncation mutants in neuroblastoma cell lines.

FIG. 7A shows the results of an IP analysis of lysates from SY5Y cells that had been transfected with GFP-tagged WT-EGFR and EGFRΔ768. FIGS. 7B and 7E shows the results of an experiment confirming the efficentcy of transfection. FIG. 7C shows the results of an RT-PCR analysis on SY5Y cells that had been transfected with GFP-tagged WT-EGFR and EGFRΔ768. FIG. 7D shows the results of an IP-western analysis to evaluate the phosphorylation status of GFP-tagged WT-EGFR and EGFRΔ768.

FIG. 10 shows the amino acid sequence of EGFRΔ768 (SEQ ID NO: 1). The highlighted segment "vcqgtcvkkcp" (SEQ ID NO: 9) denotes the amino acids at the junction of exon 2 and exon 7.

FIG. 11 shows the amino acid sequence of EGFRΔ471 (SEQ ID NO: 2). The highlighted segment "ekkgqk" (SEQ ID NO: 10) denotes the amino acids at the junction of exon 1 and exon 4.

FIG. 12 shows the amino acid sequence of EGFRΔ660 (SEQ ID NO: 3). The highlighted segment "lsffvvt" (SEQ ID NO: 11) denotes the amino acids at the junction of exon 2 and exon 8.

DETAILED DESCRIPTION

Figure 1B:
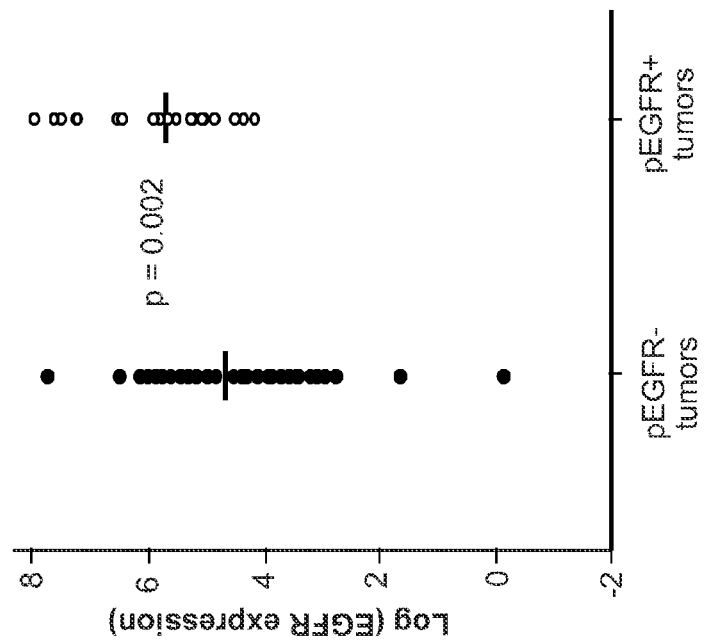
FIGS. 1A-1D show protein analysis by IPW and IHC. (A) Representative EGFR IPW analysis of HNSCC with their matched adjacent noncancerous tissues. EGF stimulated COS cells are positive controls. (B) Comparison of EGFR expression between pEGFR+ (n=22) and pEGFR− (n=34) HNSCC. EGFR expression is calculated on a logarithmic scale. Tumors with log (EGFR expression)<4 are never phosphorylated; tumors with log (EGFR expression) between 4 and 8 are variable in their receptor activity level. (C) Comparison of processing time between pEGFR+ and pEGFR− tumors. The circle represents the mean. The error bars show 95% confidence interval of the means. (D) EGFR immunohistochemistry of a representative HNSCC, D22329 (100×). Viable tumor comprised about 50% of the tissue section. Noted immunohistochemical staining is detected in tumor epithelial cells, with minimal expression in tumor stroma.

The present invention is based, in part, on our discovery of EGFR deletion mutations that encode truncated versions of the EGFR. These mutant polypeptides lack a substantial portion of the extracellular domain found in the well characterized, wild-type EGFR. As the truncated EGFR polypeptides can have an altered sensitivity to EGFR therapeutics, for example, EGFR tyrosine kinase inhibitors (TKIs), we determined that the naturally-occurring polypeptides would be useful biomarkers for detecting and/or classifying a patient's risk of developing an EGFR-related cancer; the different forms of EGFR-related cancers, including head and neck cancers and neuroblastomas; and a given cancer's stage. The polypeptides are also useful as targets for developing new chemotherapeutic agents, and can be incorporated as targets in standard screens for therapeutic agents that inhibit cell proliferation, growth, or metastasis.

The epidermal growth factor receptor (EGFR; ErbB-1; HER1 in humans) is the cell-surface receptor for members of the epidermal growth factor family (EGF-family) of extracellular protein ligands. The epidermal growth factor receptor is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4).

The EGFR gene sequence is highly conserved. The human EGFR gene is located on chromosome 7 at position 7p11.2 and spans approximately 200 kb of genomic DNA. It consists of 28 exons and encodes a 170 kDa glycoprotein that comprises three domains: an extracellular domain (encoded by exons 1-16), an intracellular domain (encoded by exons 18-28), and the membrane spanning region (encoded by exon 17). The extracellular domain has four subdomains (I-IV). The intracellular domain has a C-terminal regulatory domain and the tyrosine kinase (TK) domain. Reference sequences for the EGFR genomic sequence can be found at ENSEMBL ENSG00000146648. Exemplary references sequences for the EGFR mRNA and polypeptide sequences can be found at the NCBI GenBank data base at NM_005228.3, public GI:41327737 and NP_005219.2 GI:29725609.

Mutations in the EGFR gene are frequently found in many human tumors. The EGFRvIII mutation is an 801 base pair in-frame deletion that spans exons 2-7 of the wild type EGFR gene. The resulting aberrant transcript contains all of exon 1 followed by a sequence starting at base 3 of exon 8 (EGFRΔ801). A consequence of this deletion is the fusion of two otherwise distant portions of the EFGR molecule and the formation of a new codon (GGT) at the splice junction. The resulting truncated EGFR polypeptide thus includes a novel glycine residue flanked by animon acid sequences that are not typically adjacent in the wild-type EGFR. EGFRvIII has potent pro-oncogenic effects, is constitutively active, does not bind EGFR ligands and does not downregulate upon autophosphorylation.

We have identified a series of EGFR deletion mutations in human tumors, the nucleic acid and protein sequences of which constitute a part of our invention, together with the variant sequences described herein (e.g., gene and protein homologs from non-human sources and larger moieties, such as fusion proteins or conjugates including a truncated EGFR and expression vectors encoding them). These mutations direct the expression of novel truncated EGFR polypetides that lack substantial portions of the extracellular domain. The EGFR mutants described herein do not include EGFRvIII. The EGFRΔ768 mutation has an in-frame deletion from nucleotide 102 of exon 2 to nucleotide 869 of exon 7. This EGFRΔ768 deletion results in an mRNA transcript encoding 11 more amino acids than does the transcript that encodes EGFRvIII. The amino acid sequence of EGFRΔ768 is shown in FIG. 10 (SEQ ID NO:1). The EGFRΔ471 mutation has an in-frame deletion from nucleotide 89 of exon 1 to nucleotide 559 of exon 4. This EGFRΔ471 deletion results in an mRNA transcript that includes a new codon (GGC) at the splice junction. The new codon directs the synthesis of a glycine residue at the splice junction. The amino acid sequence of EGFRΔ471 is shown in FIG. 11 (SEQ ID NO:2). The EGFRΔ660 mutation has an in-frame deletion from nucleotide 237 of exon 2 to nucleotide 896 of exon 8. This EGFRΔ660 deletion results in an mRNA transcript that includes a new codon (UT) at the splice junction. The new codon directs the synthesis of a phenylalanine residue at the splice junction. The amino acid sequence of EGFRΔ660 is shown in FIG. 12 (SEQ ID NO:3).

Polypeptides: We refer to the amino acid-based compositions of the invention as "polypeptides" to convey that they are linear polymers of amino acid residues and to help distinguish them from full-length proteins. While the content of the polypeptides of the invention can vary as described herein, none of them have the sequence of a full-length, naturally-occurring EGFR; the polypeptides of the invention are not full-length, wild-type EGFRs nor EGFRvIII. We have stated that a polypeptide of the invention can "constitute" or "include" a fragment of an EGFR, and the invention encompasses polypeptides that constitute or include biologically active variants of the EGFRs described herein. It will be understood that the polypeptides can therefore include only a fragment of an EGFR (or a biologically active variant thereof) but may include additional residues as well.

The bonds between the amino acid residues can be conventional peptide bonds or another covalent bond (such as an ester or ether bond), and the polypeptides can be modified by amidation, phosphorylation or glycosylation. A modification can affect the polypeptide backbone and/or one or more side chains. Chemical modifications can be naturally occurring modifications made in vivo following translation of an mRNA encoding the polypeptide (e.g., glycosylation in a bacterial host) or synthetic modifications made in vitro. A biologically active variant of a truncated EGFR can include one or more structural modifications resulting from any combination of naturally occurring (i.e., made naturally in vivo) and synthetic modifications (i.e., naturally occurring or non-naturally occurring modifications made in vitro). Examples of modifications include, but are not limited to, amidation (e.g., replacement of the free carboxyl group at the C-terminus by an amino group); biotinylation (e.g., acylation of lysine or other reactive amino acid residues with a biotin molecule); glycosylation (e.g., addition of a glycosyl group to either asparagines, hydroxylysine, serine or threonine residues to generate a glycoprotein or glycopeptide); acetylation (e.g., the addition of an acetyl group, typically at the N-terminus of a polypeptide); alkylation (e.g., the addition of an alkyl group); isoprenylation (e.g., the addition of an isoprenoid group); lipoylation (e.g. attachment of a lipoate moiety); and phosphorylation (e.g., addition of a phosphate group to serine, tyrosine, threonine or histidine).

One or more of the amino acid residues in a biologically active variant may be a non-naturally occurring amino acid residue. Naturally occurring amino acid residues include those naturally encoded by the genetic code as well as non-standard amino acids (e.g., amino acids having the D-configuration instead of the L-configuration). The present peptides can also include amino acid residues that are modified versions of standard residues (e.g. pyrrolysine can be used in place of lysine and selenocysteine can be used in place of cysteine). Non-naturally occurring amino acid residues are those that have not been found in nature, but that conform to the basic formula of an amino acid and can be incorporated into a peptide. These include D-alloisoleucine(2R,3S)-2-amino-3-methylpentanoic acid and L-cyclopentyl glycine (S)-2-amino-2-cyclopentyl acetic acid. For other examples, one can consult textbooks or the worldwide web (a site is currently maintained by the California Institute of Technology and displays structures of non-natural amino acids that have been successfully incorporated into functional proteins). Non-natural amino acid residues and amino acid derivatives listed in U.S. Application No. 20040204561 (see ¶ 0042, for example) can also be used. Alternatively, or in addition, one or more of the amino acid residues in a biologically active variant can be a naturally occurring residue that differs from the naturally occurring residue found in the corresponding position in a wildtype EGFR sequence, for example P733S or R748I in exon 19. In other words, biologically active variants can include one or more amino acid substitutions. We may refer to a substitution, addition, or deletion of amino acid residues as a mutation of the wildtype sequence. As noted, the substitution can replace a naturally occurring amino acid residue with a non-naturally occurring residue or just a different naturally occurring residue. Further the substitution can constitute a conservative or non-conservative substitution. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The polypeptides that are biologically active variants of a truncated EGFR can be characterized in terms of the extent to which their sequence is similar to or identical to the corresponding truncated EGFR. For example, the sequence of a biologically active variant can be at least or about 70% identical to corresponding residues in the truncated EGFR. For example, a biologically active variant of an EGFR polypeptide can have an amino acid sequence with at least or about 70% sequence identity (e.g., at least or about 70%, 75%, 80%, 85%, 90%, 95%, 97%, 98%, or 99% sequence identity) to a truncated EGFR protein (e.g., to the amino acid sequence set forth in SEQ ID NO:1, 2 and 3 or to a homolog or ortholog thereof).

In one embodiment, the present invention features a truncated EGFR polypeptide that has been isolated or is substantially pure and that includes an amino acid sequence that is at least or about 70% identical (as noted elsewhere; at least or about 70%, 75%, 80%, 85%, 90%, 95%, 98%, or 99% identical) to the amino acid sequence of EGFRΔ768 (SEQ ID NO: 1), EGFRΔ471 (SEQ ID NO: 2) or EGFRΔ660 (SEQ ID NO: 3). The polypeptides of the invention can also be polypeptides in which the extracellular domain is at least or about 70% identical (as noted elsewhere; at least or about 70%, 75%, 80%, 85%, 90%, 95%, 98%, or 99% identical) to the amino acid sequence of EGFRΔ768 (SEQ ID NO: 1), EGFRΔ471 (SEQ ID NO: 2) or EGFRΔ660 (SEQ ID NO: 3). The remainder of the polypeptide (i.e., the transmembrane domain and/or the intracellular domain) can exhibit a similar level of variability relative to the corresponding domains of EGFRΔ768 (SEQ ID NO: 1), EGFRΔ471 (SEQ ID NO: 2) or EGFRΔ660 (SEQ ID NO: 3) or may be identical to the corresponding domains of EGFRΔ768 (SEQ ID NO: 1), EGFRΔ471 (SEQ ID NO: 2) or EGFRΔ660 (SEQ ID NO: 3).

A biologically active variant of a truncated EGFR polypeptide will retain sufficient biological activity to be useful in the present methods. The biological activity can be assessed in ways known to one of ordinary skill in the art and includes, without limitation, tumorogenicity assays in vitro and in vivo. The methods and constructs described herein for EGFRΔ768 are likewise applicable to EGFRΔ461 and EGFRΔ660. Exemplary tumorogenicity assays include cell proliferation and survival assays. For these studies, The proliferative potential of SY5Y cells expressing EGFRΔ768-GFP and EGFRvIII-GFP can be determined and compared to the parental clone expressing GFP vector alone by standard MTT assay. Briefly, the clones can be trypsinized and seeded in 96-well plate at a density of $1 \times 10^4$ cells/well. 24 hours after seeding, the cells can be treated with MTT reagent I followed by 4 hour incubation at 37° C. Next, we can add MTT reagent II and incubate the cells overnight. Cell number can be determined by spectrophotometry utilizing an ELISA plate reader at 590 nm. Each proliferation experiment can be done in triplicate. Mean number of cells will be compared among EGFRΔ768-GFP, EGFRvIII-GFP and GFP vector transfected cells using ANOVA. Next, the clones can be pretreated with irreversible or reversible EGFR inhibitor before treatment with MTT reagents. Optimal concentration of EGFR inhibitor for these experiments can be determined by biochemical analysis of the dose necessary to inhibit EGFR phosphorylation.

Then, we can analyze the survival of EGFR inhibitor treated NBL clones by flow cytometry. Treated cells with media can be collected on Day 1, 3 and 7 post EGFR inhibitor treatment. Propidium iodide (PI) can be added to an aliquot of the cell suspension. PI stained, nonviable cells will have bright red fluorescence, which can be detected with a 625/35-nm filter by flow cytometry. Each survival experiment will be done in triplicate. The number of nonviable cells per ml of culture can be determined by making a timed count of PI stained cells. Average number of nonviable cells over time can be compared between the clones.

Migration and invasion assays can also be used. We can compare the migratory and invasive potential of the EGFRΔ768-GFP, EGFRvIII-GFP and GFP vector transfected SY5Y cells using the two chambers. In a transwell filter apparatus. first, $1 \times 10^5$ cell suspension in 200 ul volume can be added to the top of the filter in the top chamber; 400 ul media without EGFR ligands can be added to the bottom chamber. After six hrs, cells will be removed; filter will be fixed and stained with DAPI. We can count the number of migrated cells per HPF for a total of 5 fields, calculate and compare the average number of migrated cells between the three groups of transfected cells. Next, cells can be pretreated with irreversible or reversible EGFR inhibitors before addition to the filter. Then, the migration experiments can be carried out as described. Each migration experiment can be done in triplicate. Comparison between the groups can be performed using ANOVA. For the cell invasion assay, we can use the modified Transwell filter apparatus to perform similar experiments as described above. The modified set up can have a homogenous layer of Matrigel on top of the filter. Instead of 6 hours, we can lengthen the time to 12 hours to allow the cells ample time to invade through the Matrigel and migrate through the filter before fixing and counting them. Each invasion experiment will also be done in triplicate. Again, comparison between the groups will be performed using ANOVA.

siRNA knockdown assays can also be used to analyse the effect of the truncated EGFRs on tumorogenicity. One can use an siRNA construct to knock down EGFRΔ768 expression in BE2M17 NBL cells. Since BE2M17 expresses both WT-EGFR and EGFRD768, the siRNA sequence should be limited to the splice junction to achieve specific knockdown of EGFRD768. Suitable siRNAs can be selected with the IDT siRNA design program. An exemplary siRNA is the splice junction 21-mer, TTGCCAAGGCACCTGCGTGAA (SEQ ID NO:4). We can transfect this sequence into BE2M17 cells and confirm knock down of EGFRΔ768 expression by real time PCR. BE2M17 cells with knock down of EGFRΔ768 can be tested for their proliferative and invasive potential in experiments as described above and compared to the parental line transfected with scramble sequence. Alternatively or in addition, 27-mer Dicer-substrate Duplex RNAs and be used since RNA duplexes in the 25-30 base length range can have as much as a 100 fold increase in potency compared to 21-mer siRNAs at the same location.

The biological activity of a truncated EGFR polypeptide can be assessed in vivo. To determine if EGFRΔ768 expression enhances tumorigenicity in vivo, we can inject EGFRΔ768-GFP, EGFRvIII-GFP and GFP vector expressing SY5Y clones subcutaneously in nude mice. The mice can be monitored for tumor formation and growth over time. They can be checked every other day by direct palpation of the injection site. The date of first palpable nodule will be recorded. Measurement in two dimensions can be taken using a caliper. The size of the tumor can be measured every other day for a total of 2 weeks or until the tumor reaches 4 cm in its longest dimension. Mice can be euthanized at the conclusion of this experiment and the tumors can be harvested for histological analysis. 2 hours prior to euthanasia of the animals, they can be injected with BrdU. Tumor sections can be stained with an anti-BrdU monoclonal antibody. Proliferation index can be calculated by the number of stained cells over the total number of cells counted in 5 high power fields. The time to tumor initiation, tumor growth over time and proliferation index between the implanted groups can be compared using ANOVA. There can be 5 mice per group.

The same groups of clonec can also be injected intravenously via tail vein into nude mice. Following injection, the mice can be imaged every two weeks over a 12 week period using the VivaCT75 microCT scanner at the Stony Brook University School of Medicine Micro-CT Facility. The mice can be given contrast materials prior to each imaging to allow for volumetric and density analysis of tumor growth in vivo. We can focus on liver and lung for the appearance of metastatic lesions. Time to the first appearance of tumor nodule can be recorded. Number of metastatic lesions can also be counted with each imaging. We can assign an index metastatic lesion for calculation of tumor volume and use this lesion for monitoring of growth over time. Animals can be euthanized at week 12. Liver and lung can be examined grossly for visible nodules and correlated with CT findings. Each nodule can be histologically confirmed as metastasis. The time to first metastatic lesion, number of metastatic foci and growth of the index lesion between the groups can be compared using ANOVA. Again, there can be 5 mice per each group.

Alternatively or in addition, a transgenic mouse model of targeted EGFRΔ768 expression in neuronal cells using the rat tyrosine hydroxylase promoter can be generated in order to analyze effects in vivo.

Biochemical analyses of signaling pathways can also be evaluated. Methods of analyzing signaling pathways are also well-known in the art and include, for example, RT-PCR analysis, gene arrays, immunoblotting, ELISA assays, Multidimensional Protein Identification Technology (MudPIT). Such analysis can involve a single gene, or multiple genes. To determine if a truncated EGFR or a variant of a truncated EGFR activates different signaling pathways than EGFRvIII or ligand activated WT-EGFR, we can use the human phospho-kinase array from R&D Systems to simultaneously screen for the activation of different downstream signaling pathways (i.e. MEK/Erk, PI3K/Akt, JNK/Jun, STAT, Chk/p53/p21, etc.). Briefly, cell extracts from EGFRΔ768-GFP and EGFRvIII-GFP expressing cells as well as EGF stimulated GFP expressing parental cells can be diluted and incubated with the arrays. The arrays can be washed and developed according to manufacture instruction. Any signaling pathways that are identified to be activated can be further investigated and validated by immunoprecipitation and western blots using commercially available antibodies for each signaling molecule.

Biologically active variants can be identified, for example, by comparing the relative activities of the variant truncated EGFR polypeptide with that of an active truncated EGFR polypeptide. Some biologically active variants may even have greater biological activity than the cognate, naturally occurring fragment. More specifically, a biologically active variant can have at least or about 30%, 40%, 50%, 60%, 70%, 80%, 90%, 95%, 98%, or more of the biological activity of the native form polypeptide.

Any cell type that is responsive to a polypeptide of the invention, or any tissue containing such responsive cells, can be used to assess biological activity, including cell lines and explants. Cell lines can be obtained from standard commercial sources and from depositories such as The American Type Culture Collection.

The polypeptides of the invention can be chemically synthesized, obtained from natural sources (insofar as they constitute fragments of a naturally occurring truncated EGFR polypeptide), or purified from cells in which they are recombinantly produced. Of course, molecular techniques can be used to express polypeptides having a sequence that is identical to a portion of a truncated EGFR polypeptide or biologically active variants thereof; the methods required for polypeptide synthesis, expression and purification are well known in the art. For example, polypeptides can be chemically synthesized using standard f-moc chemistry and purified using high pressure liquid chromatography (HPLC). Fragments of a truncated EGFR polypeptide and biologically active variants thereof can be purified by any method known in the art, including without limitation, fractionation, centrifugation, and chromatography (e.g., gel filtration, ion exchange chromatography, reverse-phase HPLC and immunoaffinity purification).

The polypeptides may be, but are not necessarily, substantially pure. A polypeptide of the invention, whether it contains a sequence that is identical to a portion of a truncated EGFR polypeptide or a biologically active variant thereof, should be considered substantially pure when it has been separated from a substantial amount of the material with which it was previously associated (e.g., cellular components where the polypeptide is recombinantly produced or reagents where the polypeptide is chemically synthesized). For example, a polypeptide of the invention is substantially pure when it is present in a composition in which it constitutes at least or about 60% of the composition by weight (e.g., at least or about 65%, 70%, 80%, 90%, 95%, or 99%). If tested by electrophoresis, a substantially pure polypeptide will yield a single major band on a non-reducing polyacrylamide gel.

To produce a recombinant polypeptide of the invention, a nucleic acid sequence encoding the polypeptide can be incorporated into (e.g., ligated into) an expression vector and used to transform a prokaryotic cell (e.g., a bacterial cell) or transfect a eukaryotic host cell (e.g., an insect, yeast, or mammalian host cell). In general, nucleic acid constructs can include one or more regulatory sequences operably linked to a nucleic acid sequence encoding a polypeptide of the invention. Regulatory sequences (e.g., promoters, enhancers, polyadenylation signals, and terminators) do not typically encode a protein/polypeptide, but instead affect the expression of a nucleic acid sequence. Such transformed or transfected cells can then be used, for example, for large or small scale production of the selected fragment of a truncated EGFR polypeptide (or a biologically active variant thereof) by methods known in the art. In essence, such methods involve culturing the cells under conditions suitable for production of the polypeptide and isolating the polypeptide from the cells or from the culture medium.

A construct can include a tag sequence designed to facilitate subsequent manipulations of the expressed nucleic acid sequence. For example, the tag can facilitate purification or localization. Tag sequences, such as green fluorescent protein (GFP), glutathione S-transferase (GST), c-myc, hemagglutinin, β-galactosidase, or Flag™ tag (Kodak) sequences are typically expressed as a fusion with the polypeptide encoded by the nucleic acid sequence. Such tags can be inserted in a nucleic acid sequence such that they are expressed anywhere along an encoded polypeptide including, for example, at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (New England Biolabs, Beverly, Mass.), and pGEN (Promega, Madison, Wis.). Additionally, representative prokaryotic expression vectors include, without limitation, pBAD (Invitrogen, Carlsbad, Calif.), the pTYB family of vectors (New England Biolabs), and pGEMEX vectors (Promega); representative mammalian expression vectors include, without limitation, pTet-On/pTet-Off (Clontech, Palo Alto, Calif.), pIND, pVAX1, pCR3.1, pcDNA3.1, pcDNA4, or pUni (Invitrogen), and pCI or pSI (Promega); representative insect expression vectors include, without limitation, pBacPAK8 or pBacPAK9 (Clontech), and p2Bac (Invitrogen); and representative yeast expression vectors include, without limitation, MATCHMAKER (Clontech) and pPICZ A, B, and C (Invitrogen).

In bacterial systems, *Escherichia coli* can be used to express a fragment of a truncated EGFR polypeptide or a biologically active variant thereof. For example, the *E. coli* strain DH10B (Invitrogen) can be transformed with the gram negative broad host range vector, pCM66 containing a nucleic acid sequence encoding a fragment of a truncated EGFR polypeptide. In another example, BL-21 cells can be transformed with a pGEX vector containing a nucleic acid sequence encoding a polypeptide of the invention. The transformed bacteria can be grown exponentially and then stimulated with isopropylthiogalactopyranoside (IPTG) prior to harvesting. In general, the polypeptides produced from a pGEX expression vector can be purified from lysed cells by adsorption to glutathione-agarose beads followed by elution in the presence of free glutathione. The pGEX vectors can be designed to include thrombin or factor Xa protease cleavage sites so that the expressed polypeptide can be released from the GST moiety.

The invention further encompasses peptidomimetics of fragments of a truncated EGFR polypeptide, which are small, protein-like polymers containing non-peptidic structural elements that are capable of mimicking or antagonizing the biological actions of a natural parent peptide (here, a fragment of a truncated EGFR polypeptide or a biologically active variant thereof). In addition to being synthetic, non-peptide compounds, peptidomimetics can have a three-dimensional conformation (i.e., a "peptide motif") that is substantially the same as the three-dimensional conformation of a selected polypeptide. The peptide motif provides the peptidomimetic compound with the ability to bind the receptor in a manner qualitatively identical to that of the parent peptide from which the peptiomimetic was derived. Peptidomimetic compounds can have additional characteristics that enhance their therapeutic utility, such as an increased biological half-life.

The peptidomimetics typically have a backbone that is partially or completely non-peptide, but with side groups that are identical to the side groups of the amino acid residues that occur in the peptide on which the peptidomimetic is based. Several types of chemical bonds (e.g., ester, thioester, thioamide, retroamide, reduced carbonyl, dimethylene and ketomethylene bonds) are known in the art to be generally useful substitutes for peptide bonds in the construction of protease-resistant peptidomimetics and can be used in the context of the present peptides).

Any peptidomimetic that has a sufficient amount of biological activity (e.g., an amount that renders the peptidomimetic experimentally or clinically useful) can be used.

As noted above in describing suitable expression vectors, the present polypeptides can include a tag, which may also be referred to as a reporter or marker (e.g., a detectable marker). A detectable marker can be any molecule that is covalently linked to the fragment of a truncated EGFR polypeptide or a biologically active fragment thereof that allows for qualitative and/or quantitative assessment of the expression or activity of the tagged peptide. The activity can include a biological activity, a physico-chemical activity, or a combination thereof. Both the form and position of the detectable marker can vary, as long as the labeled peptide retains biological activity. Many different markers can be used, and the choice of a particular marker will depend upon the desired application. Labeled polypeptides can be used, for example, for evaluating the phamacokinetics of the polypeptide both in cell-based systems and in whole animal models.

Suitable markers include, for example, enzymes, photoaffinity ligands, radioisotopes, and fluorescent or chemiluminescent compounds. Methods of introducing detectable markers into peptides are well known in the art. Markers can be added during synthesis or post-synthetically. Recombinant polypeptides can also be labeled by the addition of labeled precursors (e.g., radiolabeled amino acids) to the culture medium in which the transformed cells are grown. In some embodiments, analogues or variants of the polypeptides of the invention can be used in order to facilitate incorporation of detectable markers. For example, any N-terminal phenylalanine residue can be replaced with a closely related aromatic amino acid, such as tyrosine, that can be easily labeled with $^{125}$I. In some embodiments, additional functional groups that support effective labeling can be added to the polypeptides. For example, a 3-tributyltinbenzoyl group can be added to the N-terminus of the native structure; subsequent displacement of the tributyltin group with $^{125}$I will generate a radiolabeled iodobenzoyl group. Nucleic Acids: We may use the terms "nucleic acid" and "polynucleotide" interchangeably to refer to both RNA and DNA, including cDNA, genomic DNA, synthetic DNA, and DNA (or RNA) containing nucleic acid analogs, any of which may encode a polypeptide of the invention and all of which are encompassed by the invention. Polynucleotides can have essentially any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA) and portions thereof, transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. In the context of the present invention, nucleic acids can encode a fragment of a naturally occurring truncated EGFR polypeptide or a biologically active variant thereof.

An "isolated" nucleic acid can be, for example, a naturally-occurring DNA molecule or a fragment thereof, provided that at least one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among many (e.g., dozens, or hundreds to millions) of other nucleic acids within, for example, cDNA libraries or genomic libraries, or gel slices containing a genomic DNA restriction digest, is not an isolated nucleic acid.

Isolated nucleic acid molecules can be produced by standard techniques. For example, polymerase chain reaction (PCR) techniques can be used to obtain an isolated nucleic acid containing a nucleotide sequence described herein, including nucleotide sequences encoding a polypeptide described herein (i.e. a fragment of a truncated EGFR polypeptide or a biologically active variant thereof). PCR can be used to amplify specific sequences from DNA as well as RNA, including sequences from total genomic DNA or total cellular RNA. Various PCR methods are described in, for example, *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid (as one may wish to do, for example, when making a biologically active variant of a fragment of a truncated EGFR polypeptide).

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >50-100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring portion of a truncated EGFR polypeptide-encoding DNA (in accordance with, for example, the sequences described above).

Two nucleic acids or the polypeptides they encode may be described as having a certain degree of identity to one another. For example, a fragment of a truncated EGFR polypeptide and a biologically active variant thereof may be described as exhibiting a certain degree of identity. Alignments may be assembled by locating short CR sequences in the Protein Information Research (PIR) site. (http://pir.georgetown.edu) followed by analysis with the "short nearly identical sequences" Basic Local Alignment Search Tool (BLAST) algorithm on the NCBI website (http://www.ncbi.nlm.nih.gov/blast).

As used herein, the term "percent sequence identity" refers to the degree of identity between any given query sequence and a subject sequence. For example, a naturally occurring truncated EGFR polypeptide can be the query sequence and a fragment of a truncated EGFR polypeptide protein can be the subject sequence. Similarly, a fragment of a truncated EGFR polypeptide can be the query sequence and a biologically active variant thereof can be the subject sequence.

To determine sequence identity, a query nucleic acid or amino acid sequence can be aligned to one or more subject nucleic acid or amino acid sequences, respectively, using the computer program ClustalW (version 1.83, default parameters), which allows alignments of nucleic acid or protein sequences to be carried out across their entire length (global alignment). See Chenna et al., *Nucleic Acids Res.* 31:3497-3500, 2003.

ClustalW calculates the best match between a query and one or more subject sequences and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw). To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The nucleic acids and polypeptides described herein may be referred to as "exogenous". The term "exogenous" indicates that the nucleic acid or polypeptide is part of, or encoded by, a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

Recombinant constructs are also provided herein and can be used to transform cells in order to express a truncated EGFR polypeptide or fragment thereof. A recombinant nucleic acid construct comprises a nucleic acid encoding a fragment of a truncated EGFR polypeptide or fragment thereof as described herein, operably linked to a regulatory region suitable for expressing the a truncated EGFR polypeptide or fragment thereof in the cell. Thus, a nucleic acid can comprise a coding sequence that encodes any of the truncated EGFR polypeptides or fragment thereof as set forth in, for example, SEQ ID NOs: 1, 2 and 3. In some cases, a recombinant nucleic acid construct can include a nucleic acid comprising a coding sequence, a gene, or a fragment of a coding sequence or gene in an antisense orientation so that the antisense strand of RNA is transcribed. It will be appreciated that a number of nucleic acids can encode a polypeptide having a particular amino acid sequence. The degeneracy of the genetic code is well known in the art. For many amino acids, there is more than one nucleotide triplet that serves as the codon for the amino acid. For example, codons in the coding sequence for a given truncated EGFR polypeptide or fragment thereof can be modified such that optimal expression in a particular organism is obtained, using appropriate codon bias tables for that organism.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a host cell. For example, a marker can confer biocide resistance, such as resistance to an antibiotic (e.g., kanamycin, G418, bleomycin, or hygromycin). As noted above, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

The vector can also include a regulatory region. The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site or about 2,000 nucleotides upstream of the transcription start site. A promoter typically comprises at least a core (basal) promoter. A promoter also may include at least one control element, such as an enhancer sequence, an upstream element or an upstream activation region (UAR). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Also provided herein are antibodies that specifically recognize the EGFR truncated polypeptides of the invention. The antibodies can assume various configurations and encompass proteins consisting of one or more polypeptides substantially encoded by immunoglobulin genes. Any one of a variety of antibody structures can be used, including the intact antibody, antibody multimers, or antibody fragments or other variants thereof that include functional, antigen-binding regions of the antibody. We may use the term "immunoglobulin" synonymously with "antibody." The antibodies may be monoclonal or polyclonal in origin. Regardless of the source of the antibody, suitable antibodies include intact antibodies, for example, IgG tetramers having two heavy (H) chains and two light (L) chains, single chain antibodies, chimeric antibodies, humanized antibodies, complementary determining region (CDR)-grafted antibodies as well as antibody fragments, e.g., Fab, Fab', F(ab')2, scFv, Fv, and recombinant antibodies derived from such fragments, e.g., camelbodies, microantibodies, diabodies and bispecific antibodies.

An intact antibody is one that comprises an antigen-binding variable region ($V_H$ and $V_L$) as well as a light chain constant domain ($C_L$) and heavy chain constant domains, $C_{H1}$, $C_{H2}$ and $C_{H3}$. The constant domains may be native sequence constant domains (e.g. human native sequence constant domains) or amino acid sequence variants thereof. As is well known in the art, the $V_H$ and $V_L$ regions are further subdivided into regions of hypervariability, termed "complementarity determining regions" (CDRs), interspersed with the more conserved framework regions (FRs). The extent of the FRs and CDRs has been defined (see, Kabat et al. Sequences of Proteins of Immunological Interest, Fifth Edition, U.S. Department of Health and Human Services, NIH Publication No. 91-3242, 1991, and Chothia, et al., *J. Mol. Biol.* 196:901-917 (1987). The CDR of an antibody typically includes amino acid sequences that together define the binding affinity and specificity of the natural Fv region of a native immunoglobulin binding site.

An anti-EGFR truncated polypeptide antibody can be from any class of immunoglobulin, for example, IgA, IgG, IgE, IgD, IgM (as well as subtypes thereof (e.g., $IgG_1$, $IgG_2$, $IgG_3$, and $IgG_4$)), and the light chains of the immunoglobulin may be of types kappa or lambda. The recognized human immunoglobulin genes include the kappa, lambda, alpha ($IgA_1$ and $IgA_2$), gamma ($IgG_1$, $IgG_2$, $IgG_3$, $IgG_4$), delta, epsilon, and mu constant region genes, as well as the myriad immunoglobulin variable region genes.

The term "antigen-binding portion" of an immunoglobulin or antibody refers generally to a portion of an immunoglobulin that specifically binds to a target, in this case, an epitope comprising amino acid residues present in an EGFR truncated polypeptide but not in the wild-type EGFR polypeptide. An antigen-binding portion of an immunoglobulin is therefore a molecule in which one or more immunoglobulin chains are not full length, but which specifically binds to a cellular target. Examples of antigen-binding portions or fragments include: (i) an Fab fragment, a monovalent fragment consisting of the VLC, VHC, CL and CH1 domains; (ii) a F(ab')$_2$ fragment, a bivalent fragment comprising two Fab fragments linked by a disulfide bridge at the hinge region; (iii) a Fv fragment consisting of the VLC and VHC domains of a single arm of an antibody, and (v) an isolated CDR having sufficient framework to specifically bind, e.g., an antigen binding portion of a variable region. An antigen-binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al., *Science* 242:423-426 (1988); and Huston et al., *Proc. Natl. Acad. Sci. USA* 85:5879-5883 (1988)). Such scFvs can be a target agent of the present invention and are encompassed by the term "antigen-binding portion" of an antibody.

An "Fv" fragment is the minimum antibody fragment that contains a complete antigen-recognition and binding site. This region consists of a dimer of one heavy chain and one light chain variable domain in tight, con-covalent association. It is in this configuration that three hypervariable regions of each variable domain interact to define an antigen-binding site on the surface of the $V_H$-$V_L$ dimer. While six hypervariable regions confer antigen-binding specificity, even a single variable domain (or half of an Fv comprising only three hypervariable regions specific for an antigen) has the ability to recognize and bind antigen, although at a lower affinity than the entire binding site. To improve stability, the VH-VL domains may be connected by a flexible peptide linker such as $(Gly_4Ser)_3$ (SEQ ID NO: 12) to form a single chain Fv or scFV antibody fragment or may be engineered to form a disulfide bond by introducing two cysteine residues in the framework regions to yield a disulfide stabilized Fv (dsFv).

As noted, other useful antibody formats include diabodies, minibodies and bispecific antibodies. A diabody is a homodimer of scFvs that are covalently linked by a short peptide linker (about 5 amino acids or less). By using a linker that is too short to allow pairing between two domains on the same chain; the domains can be forced to pair with the complementary domains of another chain and create two antigen-binding sites (see, e.g., EP 404,097 and WO 93/11161 for additional information regarding diabodies). A diabody variant, $(dsFv)_2$ or a linear antibody useful in the present compositions and methods includes a pair of tandem Fd segments ($V_H$-$C_H$1-$V_H$-$C_H$1) that form a pair of antigen binding regions (see, e.g., Zapata et al., *Prot. Eng.* 8:1057 (1995)). Useful minibodies are homodimers of scFv-$C_{H3}$ fusion proteins. In the minibody variant, the Flex minibody, the scFv is fused to the hinge region of IgG1, which is in turn, linked to the $CH_3$ region by a 10-amino acid linker.

A bispecific antibody, which recognizes two different epitopes, can also be used as long as one arm specifically binds a EGFR truncated polypeptide as described herein. A variety of different bispecific antibody formats have been developed. For example, useful bispecific antibodies can be quadromas, i.e., an intact antibody in which each H-L pair is derived from a different antibody. Typically, quadromas are produced by fusion of two different B cell hybridomas, followed by screening of the fused calls to select those that have maintained the expression of both sets of clonotype immunoglobulin genes. Alternatively, a bispecific antibody can be a recombinant antibody. Exemplary formats for bispecific antibodies include, but are not limited to tandem scFvs in which two single chains of different specificity are connected via a peptide linker; diabodies and single chain diabodies.

Fragments of antibodies are suitable for use in the methods provided so long as they retain the desired specificity of the full-length antibody and/or sufficient specificity to inhibit cancer cell survival, proliferation, or metastasis. Thus, a fragment of an anti-EGFR truncated polypetide antibody, as described herein, can retain the ability of the intact antibody to bind to an epitope that is present in the EGFR truncated polypeptide and not in the wild-type EGFR polypeptide.

These antibody portions can be obtained using conventional techniques known to one of ordinary skill in the art, and the portions can be screened for utility in the same manner as intact antibodies are screened as, for example, diagnostic reagents or anti-cancer therapeutics.

Methods for preparing antibody fragments are well known in the art and encompass both biochemical methods (e.g. proteolytic digestion of intact antibodies which may be followed by chemical cross-linking) and recombinant DNA-based methods in which immunoglobulin sequences are genetically engineered to direct the synthesis of the desired fragments. Exemplary biochemical methods are described in U.S. Pat. Nos. 5,855,866; 5,877,289; 5,965,132; 6,093,399; 6,261,535; and 6,004,555. Nucleic acids encoding a chimeric or humanized chain can be expressed to produce a contiguous polypeptide. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger et al., WO 86/01533; Neuberger et al., European Patent No. 0,194,276 B1; Winter, U.S. Pat. No. 5,225,539; and Winter, European Patent No. 0,239,400 B 1. See also, Newman et al., *BioTechnology* 10:1455-1460 (1992), regarding CDR-grafted antibodies and Ladner et al. (U.S. Pat. No. 4,946,778) and Bird et al., *Science* 242:423-426 (1988)) regarding single chain antibodies.

Antibody fragments can be obtained by proteolysis of the whole immunoglobulin by the non-specific thiolprotease, papain. Papain digestion yields two identical antigen-binding fragments, termed "Fab fragments," each with a single antigen-binding site, and a residual "Fc fragment." The various fractions can be separated by protein A-Sepharose or ion exchange chromatography. The usual procedure for preparation of F(ab')$_2$ fragments from IgG of rabbit and human origin is limited proteolysis by the enzyme pepsin. Pepsin treatment of intact antibodies yields an F(ab')$_2$ fragment that has two antigen-combining sites and is still capable of cross-linking antigen. A Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. F(ab')$_2$ antibody fragments were originally produced as pairs of Fab' fragments that have hinge cysteines between them. Other chemical couplings of antibody fragments are known.

Also within the scope of the present invention are methods of making a targeting agent (e.g., an antibody or an antigen-binding fragment or other variant thereof) that targets an EGFR truncated polypeptide by, for example, specifically binding to an epitope that is present in the EGFR truncated polypeptide but not in the wild-type EGFR polypeptide. For example, variable regions can be constructed using PCR mutagenesis methods to alter DNA sequences encoding an immunoglobulin chain (e.g., using methods employed to generate humanized immunoglobulins; see e.g., Kanunan et al., *Nucl. Acids Res.* 17:5404 (1989); Sato et al., *Cancer Research* 53:851-856 (1993); Daugherty et al., *Nucleic Acids Res.* 19(9):2471-2476 (1991); and Lewis and Crowe, *Gene* 101: 297-302 (1991)). Using these or other suitable methods, variants can also be readily produced. For example, in one embodiment, cloned variable regions can be mutagenized, and sequences encoding variants with the desired specificity can be selected (e.g., from a phage library; see e.g., Krebber et al., U.S. Pat. No. 5,514,548; and Hoogenboom et al., WO 93/06213).

Other suitable methods of producing or isolating immunoglobulins that specifically recognize a cellular target as described herein include, for example, methods that rely upon immunization of transgenic animals (e.g., mice) capable of producing a full repertoire of human antibodies (see e.g., Jakobovits et al., *Proc. Natl. Acad. Sci. USA* 90:2551-2555 (1993); Jakobovits et al., *Nature* 362:255-258 (1993); Lonberg et al., U.S. Pat. No. 5,545,806; and Surani et al., U.S. Pat. No. 5,545,807).

As is well known in the art, monoclonal antibodies are homogeneous antibodies of identical antigenic specificity produced by a single clone of antibody-producing cells, and polyclonal antibodies generally recognize different epitopes on the same antigen and are produced by more than one clone of antibody producing cells. Each monoclonal antibody is directed against a single determinant on the antigen. The modifier, monoclonal, indicates the character of the antibody as being obtained from a substantially homogeneous population of antibodies, and is not to be construed as requiring production of the antibody by any particular method. For example, the monoclonal antibodies may be made by the hybridoma method first described by Kohler et al., (*Nature* 256:495 (1975)) or by recombinant DNA methods (see, e.g., U.S. Pat. No. 4,816,567). The monoclonal antibodies may also be isolated from phage antibody libraries using the techniques described in Clackson et al. (*Nature* 352:624-628 (1991)) and Marks et al., (*J. Mol. Biol.* 222:581-597 (1991)), for example.

The monoclonal antibodies herein can include chimeric antibodies, i.e., antibodies that typically have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)). Chimeric antibodies of interest include primatized antibodies comprising variable domain antigen-binding sequences derived from a non-human primate (e.g. apes, Old World monkeys, New World monkeys, prosimians) and human constant region sequences.

Various methods for generating monoclonal antibodies (mAbs) are well known in the art. See, e.g., the methods described in U.S. Pat. No. 4,196,265, incorporated herein by reference. The most standard monoclonal antibody generation techniques generally begin along the same lines as those for preparing polyclonal antibodies (*Antibodies: A Laboratory Manual*, Cold Spring Harbor Laboratory Press, Cold Spring Harbor, N.Y. (1988)). Typically, a suitable animal can be immunized with a selected immunogen to stimulate antibody-producing cells. Rodents such as mice and rats are exemplary animals, although rabbits, sheep, frogs, and chickens can also be used. Mice can be particularly useful (e.g., BALB/c mice are routinely used and generally give a higher percentage of stable fusions).

Following immunization, somatic cells with the potential for producing the desired antibodies, specifically B lymphocytes (B cells), can be selected for use in MAb generation and fusion with cells of an immortal myeloma cell, generally one of the same species as the animal that was immunized. Myeloma cell lines suited for use in hybridoma-producing fusion procedures typically are non-antibody-producing, have high fusion efficiency, and enzyme deficiencies that render then incapable of growing in certain selective media which support the growth of only the desired fused cells (hybridomas). Any one of a number of myeloma cells can be used, as are known to those of skill in the art. For example, where the immunized animal is a mouse, one can use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one can use R210.RCY3, Y3-Ag 1.2.3, IR983F, 4B210 or one of the above listed mouse cell lines. U-266, GM1500-GRG2, LICR-LON-HMy2 and UC729-6, all can be useful in connection with human cell fusions.

This culturing can provide a population of hybridomas from which specific hybridomas can be selected, followed by serial dilution and cloning into individual antibody producing lines, which can be propagated indefinitely for production of antibody.

Methods for producing monoclonal antibodies can include purification steps. For example, the antibodies can generally can be further purified, for example, using filtration, centrifugation and various chromatographic methods, such as HPLC or affinity chromatography, all of which are techniques well known to one of ordinary skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

The anti-EGFR truncated polypeptide antibodies of the invention may include CDRs from a human or non-human source. "Humanized" antibodies are generally chimeric or mutant monoclonal antibodies from mouse, rat, hamster, rabbit or other species, bearing human constant and/or variable region domains or specific changes. Techniques for generating a so-called "humanized" antibody are well known to those of skill in the art.

The framework of the immunoglobulin can be human, humanized, or non-human (e.g., a murine framework modified to decrease antigenicity in humans), or a synthetic framework (e.g., a consensus sequence). Humanized immunoglobulins are those in which the framework residues correspond to human germline sequences and the CDRs result from V(D)J recombination and somatic mutations. However, humanized immunoglobulins may also comprise amino acid residues not encoded in human germline immunoglobulin nucleic acid sequences (e.g., mutations introduced by random or site-specific mutagenesis ex vivo). It has been demonstrated that in vivo somatic mutation of human variable genes results in mutation of framework residues (see *Nature Immunol.* 2:537 (2001)). Such an antibody would be termed "human" given its source, despite the framework mutations. Mouse antibody variable domains also contain somatic mutations in framework residues (See *Sem. Immunol.* 8:159 (1996)). Consequently, transgenic mice containing the human Ig locus produce immunoglobulins that are commonly referred to as "fully human," even though they possess an average of 4.5 framework mutations (*Nature Genet.* 15:146-56 (1997)). Accepted usage therefore indicates that an antibody variable domain gene based on germline sequence but possessing framework mutations introduced by, for example, an in vivo somatic mutational process is termed "human."

Humanized antibodies may be engineered by a variety of methods known in the art including, for example: (1) grafting the non-human complementarity determining regions (CDRs) onto a human framework and constant region (a process referred to in the art as humanizing), or, alternatively, (2) transplanting the entire non-human variable domains, but providing them with a human-like surface by replacement of surface residues (a process referred to in the art as veneering). Humanized antibodies can include both humanized and veneered antibodies. Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); Lonberg and Huszar, *Intern. Rev. Immunol.* 13:65-93 (1995); Jones et al., *Nature* 321:522-525 (1986); Morrison et al., *Proc. Natl. Acad. Sci, USA,* 81:6851-6855 (1984); Morrison and Oi, *Adv. Immunol.,* 44:65-92 (1988); Verhoeyer et al., *Science* 239:1534-1536 (1988); Padlan, *Molec. Immun.* 28:489-498 (1991); Padlan, *Molec. Immunol.* 31(3):169-217 (1994); and Kettleborough, C. A. et al., *Protein Eng.* 4(7):773-83 (1991)).

In addition to chimeric and humanized antibodies, fully human antibodies can be derived from transgenic mice having human immunoglobulin genes (see, e.g., U.S. Pat. Nos. 6,075,181; 6,091,001; and 6,114,598), or from phage display libraries of human immunoglobulin genes (see, e.g. McCafferty et al., *Nature* 348:552-554 (1990); Clackson et al., *Nature* 352:624-628 (1991), and Marks et al., *J. Mol. Biol.* 222:581-597 (1991)). In some embodiments, antibodies may be produced and identified by scFv-phage display libraries using standard methods known in the art.

The anti-EGFR truncated polypeptide antibodies may be modified to modulate their antigen binding affinity, their effector functions, or their pharmacokinetics. In particular, random mutations can be made in the CDRs and products screened to identify antibodies with higher affinities and/or higher specificities. Such mutagenesis and selection is routinely practiced in the antibody arts. A convenient way for generating such substitutional variants is affinity maturation using phage display.

CDR shuffling and implantation technologies can be used with the antibodies provided herein, for example. CDR shuffling inserts CDR sequences into a specific framework region (Jirholt et al., *Gene* 215:471 (1988)). CDR implantation techniques permit random combination of CDR sequences into a single master framework (Soderlind et al., *Immunotechnol.* 4:279 (1999); and Soderlind et al., *Nature Biotechnol.* 18:852 (2000)). Using such techniques, CDR sequences of the anti-EGFR truncated polypeptide antibodies, for example, can be mutagenized to create a plurality of different sequences, which can be incorporated into a scaffold sequence and the resultant antibody variants screened for desired characteristics, e.g., higher affinity. In some embodiments, sequences of the anti-EGFR truncated polypeptide antibodies can be examined for the presence of T cell epitopes, as is known in the art. The underlying sequence can then be changed to remove T cell epitopes, i.e., to "deimmunize" the antibody.

Recombinant technology using, for example phagemid technology, allows for preparation of antibodies having a desired specificity from recombinant genes encoding a range of antibodies. Certain recombinant techniques involve isolation of antibody genes by immunological screening of combinatorial immunoglobulin phage expression libraries prepared from RNA isolated from spleen of an immunized animal (Morrison et al., *Mt. Sinai J. Med.* 53:175 (1986); Winter and Milstein, *Nature* 349:293 (1991); Barbas et al., *Proc. Natl. Acad. Sci. USA* 89:4457 (1992)). For such methods, combinatorial immunoglobulin phagemid libraries can be prepared from RNA isolated from spleen of an immunized animal, and phagemids expressing appropriate antibodies can be selected by panning using cells expressing antigen and control cells. Advantage of this approach over conventional hybridoma techniques include approximately $10^4$ times as many antibodies can be produced and screened in a single round, and that new specificities can be generated by H and L chain combination, which can further increase the percentage of appropriate antibodies generated.

One method for the generation of a large repertoire of diverse antibody molecules in bacteria utilizes the bacteriophage lambda as the vector (Huse et al., Science 246:1275 (1989)). Production of antibodies using the lambda vector involves the cloning of heavy and light chain populations of DNA sequences into separate starting vectors. Vectors subsequently can be randomly combined to form a single vector that directs co-expression of heavy and light chains to form antibody fragments. The general technique for filamentous phage display is described (U.S. Pat. No. 5,658,727). In a most general sense, the method provides a system for the simultaneous cloning and screening of pre-selected ligand-binding specificities from antibody gene repertoires using a single vector system. Screening of isolated members of the library for a pre-selected ligand-binding capacity allows the correlation of the binding capacity of an expressed antibody molecule with a convenient means to isolate a gene that encodes the member from the library. Additional methods for screening phagemid libraries are described (U.S. Pat. Nos. 5,580,717; 5,427,908; 5,403,484; and 5,223,409).

One method for the generation and screening of large libraries of wholly or partially synthetic antibody combining sites, or paratopes, utilizes display vectors derived from filamentous phage such as M13, fl or fd (U.S. Pat. No. 5,698,426, incorporated herein by reference). Filamentous phage display vectors, referred to as "phagemids," yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries (Kang et al., Proc. Natl. Acad. Sci. USA 88:4363 (1991); and Barbas et al., Proc. Natl. Acad. Sci. USA 88:7978 (1991)). The surface expression library is screened for specific Fab fragments that bind neuraminidase molecules by standard affinity isolation procedures. The selected Fab fragments can be characterized by sequencing the nucleic acids encoding the polypeptides after amplification of the phage population.

One method for producing diverse libraries of antibodies and screening for desirable binding specificities is described (U.S. Pat. Nos. 5,667,988 and 5,759,817). The method involves the preparation of libraries of heterodimeric immunoglobulin molecules in the form of phagemid libraries using degenerate oligonucleotides and primer extension reactions to incorporate degeneracies into CDR regions of immunoglobulin variable heavy and light chain variable domains, and display of mutagenized polypeptides on the surface of the phagemid. Thereafter, the display protein is screened for the ability to bind to a preselected antigen. A further variation of this method for producing diverse libraries of antibodies and screening for desirable binding specificities is described U.S. Pat. No. 5,702,892, incorporated herein by reference). In this method, only heavy chain sequences are employed, heavy chain sequences are randomized at all nucleotide positions that encode either the CDRI or CDRIII hypervariable region, and the genetic variability in the CDRs can be generated independent of any biological process.

In addition to the combinatorial immunoglobulin phage expression libraries disclosed above, one molecular cloning approach is to prepare antibodies from transgenic mice containing human antibody libraries. Such techniques are described (U.S. Pat. No. 5,545,807, incorporated herein by reference). Such transgenic animals can be employed to produce human antibodies of a single isotype, more specifically an isotype that is essential for B cell maturation, such as IgM and possibly IgD. Another method for producing human antibodies is described in U.S. Pat. Nos. 5,545,806; 5,569,825; 5,625,126; 5,633,425; 5,661,016; and 5,770,429, wherein transgenic animals are described that are capable of switching from an isotype needed for B cell development to other isotypes.

The anti-EGFR truncated polypeptide antibodies may be modified to reduce or abolish glycosylation. An immunoglobulin that lacks glycosylation may be an immunoglobulin that is not glycosylated at all; that is not fully glycosylated; or that is atypically glycosylated (i.e., the glycosylation pattern for the mutant differs from the glycosylation pattern of the corresponding wild type immunoglobulin). The IgG polypeptides include one or more (e.g., 1, 2, or 3 or more) mutations that attenuate glycosylation, i.e., mutations that result in an IgG CH2 domain that lacks glycosylation, or is not fully glycosylated or is atypically glycosylated. Mutations of the asparagine residue at amino acid 297 in human IgG1 is an example of such a mutation. The oligosaccharide structure can also be modified, for example, by eliminating the fusose moiety from the N-linked glycan.

Antibodies can also be modified to increase their stability and or solubility in vivo by conjugation to non-protein polymers, e.g, polyethylene glycol. Any PEGylation method can be used as long as the anti-EGFR truncated polypeptide antibody retains the ability to selectively bind the EGFR truncated polypeptide.

A wide variety of antibody/immunoglobulin frameworks or scaffolds can be employed so long as the resulting polypeptide includes at least one binding region that is specific for the target, i.e., the EGFR truncated polypeptide. Such frameworks or scaffolds include the five main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard.

One can generate non-immunoglobulin based antibodies using non-immunoglobulin scaffolds onto which CDRs of the anti-EGFR truncated polypeptide antibody can be grafted. Any non-immunoglobulin framework and scaffold know to those in the art may be used, as long as the framework or scaffold includes a binding region specific for the target. Immunoglobulin-like molecules include proteins that share certain structural features with immunoglobulins, for example, a β-sheet secondary structure. Examples of non-immunoglobulin frameworks or scaffolds include, but are not limited to, adnectins (fibronectin), ankyrin, domain antibodies and Ablynx nv, lipocalin, small modular immuno-pharmaceuticals (Trubion Pharmaceuticals Inc., Seattle, Wash.), maxybodies (Avidia, Inc., Mountain View, Calif.), Protein A and affilin (gamma-crystallin or ubiquitin) (Scil Proteins GmbH, Halle, Germany).

The anti-EGFR truncated polypeptide antibody of the invention specifically bind to an epitope on an EGFR truncated polypeptide but not on the wild-type EGFR. An epitope refers to an antigenic determinant on a target that is specifically bound by the paratope, i.e., the binding site of an antibody. Epitopic determinants usually consist of chemically active surface groupings of molecules such as amino acids or sugar side chains, and typically have specific three-dimensional structural characteristics, as well as specific charge characteristics. Epitopes generally have between about 4 to about 10 contiguous amino acids (a continuous epitope), or alternatively can be a set of noncontiguous amino acids that define a particular structure (e.g., a conformational epitope). Thus, an epitope can consist of at least 4, at least 6, at least 8, at least 10, and at least 12 such amino acids. Methods of determining the spatial conformation of amino acids are known in the art, and include, for example, x-ray crystallography and 2-dimensional nuclear magnetic resonance.

The method of making anti-EGFR truncated polypeptide antibodies will vary, but in general, the immunogen will include an amino acid segment that is present in the EGFR truncated polypeptide but not on the wild-type EGFR polypeptide. Useful regions include the splice junctions of the EGFR truncated polypeptides. For example, for the EGFRΔ768 polypeptide, suitable immunogens would be located in amino acids that are encoded by the sequence at the splice junction between nucleotide 102 of exon 2 to nucleotide 869 of exon 7. For the EGFRΔ471 polypeptide, suitable immunogens would be located in amino acids that are encoded by the sequence at the splice junction between nucleotide 89 of exon 1 to nucleotide 559 of exon 4 and would include the glycine residue created by the splicing event. For the EGFRΔ660 polypeitde, suitable immunogens would be located in amino acids that are encoded by the sequence at the splice junction between nucleotide 237 of exon 2 to nucleotide 896 of exon 8 and would include the phenylalanine residue created by the splicing event.

Methods of predicting other potential epitopes to which an antibody can bind are well-known to those of skill in the art and include without limitation, Kyte-Doolittle Analysis (Kyte and Dolittle, *J. Mol. Biol.* 157:105-132 (1982)), Hopp and Woods Analysis (Hopp and Woods, *Proc. Natl. Acad. Sci. USA* 78:3824-3828 (1981); Hopp and Woods, *Mol. Immunol.* 20:483-489 (1983); Hopp, *J. Immunol. Methods* 88:1-18 (1986)), Jameson-Wolf Analysis (Jameson and Wolf, *Comput. Appl. Biosci.* 4:181-186 (1988)), and Emini Analysis (Emini et al., *Virology* 140:13-20 (1985)). In some embodiments, potential epitopes are identified by determining theoretical extracellular domains. Analysis algorithms such as TMpred (see Hofmann and Stoffel, *Biol. Chem.* 374:166 (1993)) or TMHMM (Krogh et al., *J. Mol. Biol.*, 305(3):567-580 (2001)) can be used to make such predictions. Other algorithms, such as SignalP 3.0 (Bednsten et al., *J. Mol. Biol.* 340(4):783-795 (2004)) can be used to predict the presence of signal peptides and to predict where those peptides would be cleaved from the full-length protein. The portions of the proteins on the outside of the cell can serve as targets for antibody interaction.

The compositions of the present invention include antibodies that (1) exhibit a threshold level of binding activity; and/or (2) do not significantly cross-react with known related polypeptide molecules. The binding affinity of an antibody can be readily determined by one of ordinary skill in the art, for example, by Scatchard analysis (Scatchard, *Ann. NY Acad, Sci.* 51:660-672 (1949)).

In some embodiments, the anti-EGFR truncated polypeptide antibodies can bind to their target epitopes or mimetic decoys at least 1.5-fold, 2-fold, 5-fold 10-fold, 100-fold, $10^3$-fold, $10^4$-fold, $10^5$-fold, $10^6$-fold or greater for the target EGFR truncated polypeptide than to other proteins predicted to have some homology to the EGFR truncated polypeptide.

In some embodiments the anti-EGFR truncated polypeptide antibodies bind with high affinity of $10^{-4}$M or less, $10^{-7}$M or less, $10^{-9}$M or less or with subnanomolar affinity (0.9, 0.8, 0.7, 0.6, 0.5, 0.4, 0.3, 0.2, 0.1 nM or even less). In some embodiments the binding affinity of the antibodies for the EGFR truncated polypeptide is at least $1 \times 10^6$ Ka. In some embodiments the binding affinity of the antibodies for the EGFR truncated polypeptide is at least $5 \times 10^6$ Ka, at least $1 \times 10^7$ Ka, at least $2 \times 10^7$ Ka, at least $1 \times 10^8$ Ka, or greater. Antibodies may also be described or specified in terms of their binding affinity to the EGFR truncated polypeptide. In some embodiments binding affinities include those with a Kd less than $5 \times 10^{-2}$ M, $10^{-2}$ M, $5 \times 10^{-3}$ M, $10^{-3}$ M, $5 \times 10^{-3}$M, $10^{-4}$ M, $5 \times 10^{-5}$ M, $10^{-5}$ M, $5 \times 10.^{-6}$ M, $10^{-6}$ M, $5 \times 10^{-7}$ M, $10.^{-7}$M, $5 \times 10.^{-8}$ M, $10^{-8}$M, $5 \times 10.^{-9}$M, $5 \times 10.^{-10}$ M, $10^{-10}$M, $5 \times 10^{-11}$ M, $10^{-11}$M, $5 \times 10^{-12}$M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M, or less.

In some embodiments, the antibodies do not bind to known related polypeptide molecules; for example, they bind the EGFR truncated polypeptide but not known related polypeptides. Antibodies may be screened against known related polypeptides to isolate an antibody population that specifically binds to an EGFR truncated polypeptide but not to wild-type EGFR polypeptide or an EGFRvIII polypeptide. For example, antibodies specific to an EGFR truncated polypeptide will flow through a column comprising a wild-type EGFR polypeptide adhered to insoluble matrix under appropriate buffer conditions. Such screening allows isolation of polyclonal and monoclonal antibodies non-crossreactive to closely related polypeptides (Antibodies: A Laboratory Manual, Harlow and Lane (eds.), Cold Spring Harbor Laboratory Press, 1988; Current so Protocols in Immunology, Cooligan et al. (eds.), National Institutes of Health, John Wiley and Sons, Inc., 1995). Screening and isolation of specific antibodies is well known in the art (see, Fundamental Immunology, Paul (eds.), Raven Press, 1993; Getzoff et al., *Adv. in Immunol.* 43:1-98 (1988); Monoclonal Antibodies: Principles and Practice, Goding, J. W. (eds.), Academic Press Ltd., 1996; Benjamin et al., *Ann. Rev. Immunol.* 2:67-101, 1984). Representative examples of such assays include: concurrent immunoelectrophoresis, radioimmunoassay (RIA), radioimmunoprecipitation, enzyme-linked immunosorbent assay (ELISA), dot blot or Western blot assay, inhibition or competition assay, and sandwich assay.

The anti-EGFR truncated polypeptide antibodies can include a tag, which may also be referred to as a reporter or marker (e.g., a detectable marker). A detectable marker can be any molecule that is covalently linked to anti-EGFR truncated polypeptide antibody or a biologically active fragment thereof that allows for qualitative and/or quantitative assessment of the expression or activity of the tagged peptide. The activity can include a biological activity, a physico-chemical activity, or a combination thereof. Both the form and position of the detectable marker can vary, as long as the labeled antibody retains biological activity. Many different markers can be used, and the choice of a particular marker will depend upon the desired application. Labeled anti-EGFR truncated polypeptide antibodies can be used, for example, for assessing the levels of EGFR truncated polypeptide in a biological sample, e.g., urine, saliva, cerebrospinal fluid, blood or a biopsy sample or for evaluation the clinical response to an EGFR therapeutic.

Suitable markers include, for example, enzymes, photoaffinity ligands, radioisotopes, and fluorescent or chemiluminescent compounds. Methods of introducing detectable markers into peptides are well known in the art. Markers can be added during synthesis or post-synthetically. Recombinant anti-EGFR truncated polypeptide antibodies or biologically active variants thereof can also be labeled by the addition of labeled precursors (e.g., radiolabeled amino acids) to the culture medium in which the transformed cells are grown. In some embodiments, analogues or variants of peptides can be used in order to facilitate incorporation of detectable markers. For example, any N-terminal phenylalanine residue can be replaced with a closely related aromatic amino acid, such as tyrosine, that can be easily labeled with $^{125}$I. In some embodiments, additional functional groups that support effective labeling can be added to the fragments of an anti-EGFR truncated polypeptide antibody or biologically active variants thereof. For example, a 3-tributyltinbenzoyl group can be added to the N-terminus of the native structure; subsequent displacement of the tributyltin group with $^{125}$I will generate a radiolabeled iodobenzoyl group.

In lieu of administering an antibody or antibody-like therapeutic per se, the present methods can also be carried out by administering a protein that elicits the production of anti-EGFR truncated polypeptide antibodies in vivo. Accordingly, the compositions of the invention include antigenic fragments of the splice junction of the EGFR truncated polypeptides. These polypeptides can be fused to a heterologous polypeptide to generate an immunogenic fusion protein.

The compositions disclosed herein are generally and variously useful for treatment of cancer. More specifically, the compositions and methods provided herein can allow clinicians to provide effective indivualized therapies for cancer. The compositions may be used as diagnostic reagents to assist in determining a course of treament, for example to distinguish those patients who are most likely to benefit from receiving certain anti-cancer agents from those who are least likely to benefit from receiving those same anti-cancer agents. For example, the EGFR truncated polypeptides described herein alter the sensitivity of the EGFR to EGFR TKI inhibitors gefinitib, erlotinib or cetuximab. Confirmation that a patient does or does not express a EGFR truncated polypeptide will permit the attending clinician to modify or adjuct the course of treament accordingly.

The compositions described herein are also useful as therapeutics. For example, antibodies that are selective for an EGFR truncated polypeptide may be useful therapeutics in treating tumors that are resistant to conventional EGFR TKI inhibitors, for example, for example, gefinitib, erlotinib or cetuximab.

A patient is effectively treated whenever a clinically beneficial result ensues. This may mean, for example, a complete resolution of the symptoms of a disease, a decrease in the severity of the symptoms of the disease, or a slowing of the disease's progression. These methods can further include the steps of a) identifying a subject (e.g., a patient and, more specifically, a human patient) who has cancer; and b) providing to the subject a composition comprising a compound described herein, such as any pharmaceutically acceptable salt of such a compound. a complete resolution of the symptoms of a disease, a decrease in the severity of the symptoms of the disease, or a slowing of the disease's progression. These methods can further include the steps of a) identifying a subject (e.g., a patient and, more specifically, a human patient) who has cancer; and b) providing to the subject a composition comprising a compound described herein, such as any pharmaceutically acceptable salt of such a compound. An amount of such a compound provided to the subject that results in a complete resolution of the symptoms of a disease, a decrease in the severity of the symptoms of the disease, or a slowing of the disease's progression is considered a therapeutically effective amount. The present methods may also include a monitoring step to help optimize dosing and scheduling as well as predict outcome. For example, monitoring can be used to detect the onset of drug resistance and to rapidly distinguish responsive patients from nonresponsive patients. Where there are signs of resistance or nonresponsiveness, a physician can choose an alternative or adjunctive agent before the tumor develops additional escape mechanisms.

Patients amenable to the methods described herein include patients with head and neck squamous cell carcinomas and neuroblstomas. Also included are any of a variety of cancers or neoplastic disorders associated with misregulation of EGFR expression or activity. EGFR overexpression (known as upregulation) or overactivity have been associated with a number of cancers, including lung cancer, anal cancers and glioblastoma multiforme. Mutations, amplifications or misregulations of EGFR or family members are implicated in about 30% of all epithelial cancers. Exemplary forms of cancer include for example, without limitation, breast cancer, hematological cancers such as myeloma, leukemia and lymphoma (e.g., Burkitt lymphoma, non-Hodgkin lymphoma, Hodgkin lymphoma, and acute T cell leukemia) neurological tumors such as brain tumors, e.g., gliomas, including astrocytomas or glioblastomas, melanomas, lung cancer, head and neck cancer, thyroid cancer, gastrointestinal tumors such as stomach, colon or rectal cancer, liver cancer, pancreatic cancer, genitourinary tumors such ovarian cancer, vaginal cancer, vulval cancer, endometrial cancer, bladder cancer, kidney cancer, testicular cancer, prostate cancer, or penile cancer, bone tumors, vascular tumors, and skin cancers such as basal cell carcinoma, squamous cell carcinoma and melanoma.

The methods disclosed herein can be applied to a wide range of species, e.g., humans, non-human primates (e.g., monkeys), horses or other livestock, dogs, cats or other mammals kept as pets, rats, mice, or other laboratory animals. The compositions described herein are useful in diagnostic and therapeutic compositions and regimens or for the manufacture of a medicament for use in treatment of diseases or conditions as described herein (e.g., a cancer disclosed herein).

The compostions described herein e.g., anti-EGFR truncated polypeptide antibodies, anti-sense oligonucleotides or siRNA can be administered directly to a mammal, which we may also refer to as a "subject" or "patient." Generally, the compostions can be suspended in a pharmaceutically acceptable carrier (e.g., physiological saline or a buffered saline solution) to facilitate their delivery (e.g., by intravenous administration).

Regardless of their original source or the manner in which they are obtained, the compositions of the invention can be formulated in accordance with their use. For example, the compositions can be formulated within compositions for application to cells in tissue culture or for administration to a patient. When employed as pharmaceuticals, any of the present compositions can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, one or more of the compositions described herein in combination with one or more pharmaceutically acceptable carriers. In making the compositions of the invention, the active ingredient is typically mixed with an excipient, diluted by an excipient or enclosed within such a carrier in the form of, for example, a capsule, tablet, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. As is known in the art, the type of diluent can vary depending upon the intended route of administration. The resulting compositions can include additional agents, such as preservatives. The compositions may also be applied to a surface of a device (e.g., a catheter) or contained within a pump, patch, or other drug delivery device. The compositions of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in Remington's Pharmaceutical Sciences (E. W. Martin), a well-known reference text in this field, and in the USP/NF (United States Pharmacopeia and the National Formulary).

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein and/or known in the art. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner. The compositions administered to a patient can be in the form of one or more of the pharmaceutical compositions described above. These compositions can be sterilized by conventional sterilization techniques or may be sterile filtered. Aqueous solutions can be packaged for use as is, or lyophilized, the lyophilized preparation being combined with a sterile aqueous carrier prior to administration. The pH of the compound preparations typically will be between about 3 and 11, for example, between about 5 to 9, between 6 and 7, between 7 and 8. It will be understood that use of certain of the foregoing excipients, carriers, or stabilizers could result in the formation of pharmaceutical salts.

The proportion or concentration of the compounds of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration.

The therapeutic dosage of the compounds of the present invention can vary according to, for example, the particular use for which the treatment is made, the manner of administration of the compound, the health and condition of the patient, and the judgment of the attending clinician. The proportion or concentration of a compound of the invention in a pharmaceutical composition can vary depending upon a number of factors including dosage, chemical characteristics (e.g., hydrophobicity), and the route of administration. For example, the compositions of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. In some embodiments, the dose can be, for example, 1 mg/kg, 2 mg/kg, 5 mg/kg, 10 mg/kg, 20 mg/kg, 50 mg/kg or 100 mg/kg. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Any composition described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinicians. Suitable dosages are in the range of 0.01-1,000 mg/kg. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the compounds in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, a compound can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compounds can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

The compounds may also be administered with another therapeutic agent, such as a cytotoxic agent, a cancer chemotherapeutic or other therapeutic antibodies, e.g., antibodies that recognize additional cellular targets. Concurrent administration of two or more therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The compostions of the invention are also useful in the development of screening assays for identification of agents that may be active against the EGFR truncated polypetides of the invention. The exact format of the assay can vary widely, but may indluce identification of agents that inhibit phosphorylation of a truncated EGFR polypeptide. Such methods could include providing a polypeptide comprising an amino acid sequence at least 80% identical to EGFRΔ768 (SEQ ID NO: 1), EGFRΔ471 (SEQ ID NO: 2) or EGFRΔ660 (SEQ ID NO: 3); contacting the polypeptide and a test compound; and determining whether the phosphorylation of the truncated EGFR polypeptide is decreased in the presence of the test compound, wherein a decrease in phosphorylation is an indication that the test compound inhibits phosphorylation of the truncated EGFR polypeptide.

EXAMPLES

Example 1

Materials and Methods

The work described below was conducted to explore our belief that EGFR and tumor staging correlates when different aspects of the receptor are evaluated in combination. We used different molecular methods to examine the various aspects of EGFR in the primary tumors. These included immunoprecipitation followed by Western blotting (IPW), immunohistochemistry (IHC) and reverse transcriptase polymerase chain reaction (RT-PCR) coupled with DNA sequencing. The advantage of using multiple techniques to examine the status of an oncogenic receptor is most apparent from the correlation study linking HER-2 to survival in breast cancer (Slamon et al., Science, 244:707-712, 1989). We analyzed EGFR in a total of 60 primary HNSCC samples using a combination of IPW, IHC and RT-PCR. We found that the combination of phosphorylated and truncated EGFR correlates with advanced tumor and nodal stage in head and neck cancers. In addition, we discovered three novel EGFR truncations and two missense kinase mutations in these tumors.

Collection of Primary Human Tumors: Fresh, frozen primary human tumors were collected prospectively for this study through the National Cancer Institute (NCl) sponsored Cooperative Human Tissue Network (CHTN). When head and neck cancer patients presented to the CHTN institutions for surgery, informed consent for participation in research using excess tumor tissues was obtained by the CHTN staff at the local institutions. Once patients consented, our team would be notified of the tumor arrival. At the time of procurement, the CHTN staff also reviewed patients' medical charts to obtain relevant clinical information such as age, sex, race, prior treatment, imaging reports, history of smoking and alcohol use. Detail pathology reports included information such as tumor location, nodal involvement, size and number of involved nodes, histologic features and staging were sent to our team at the same time. These reports were standardized across institutions. In addition, the time from surgical excision of the tumor to storage in liquid nitrogen was recorded and provided by the CHTN for each tumor. All frozen tumors were shipped in dry ice, archived and stored in our lab. Institutional Review Board (IRB) approval for the study was obtained at our institution. One H&E stained and 10 unstained slides from each specimen were received at the same time. The following criteria were established for inclusion in our correlation analysis. Only histologically confirmed head and neck squamous cell carcinomas of the primary sites will be included and tumors with cancer to stroma ratio of ≤10% will be excluded to avoid false negative results.

Processing of Primary Tumors for Protein and RNA Analyses: Primary tumors were homogenized in 1 ml of Triton X lysis buffer (50 mM Tris-Cl, pH=8, 150 mM NaCl and 1% Triton X-100) with protease inhibitor and sodium orthovanadate using the POLYTRON system PT 10-35 GT (Kinematica AG). The homogenates were spun down; pellets were discarded and the supernatants were saved for protein analyses. Separate pieces of the frozen tumor were homogenized in 1 ml of Trizol Reagent using the POLYTRON system PT 1200 E (Kinematica AG). Total RNA was isolated per manufacturer recommendation (Life Technologies). Protein concentrations were determined by Bradford assay. RNA concentration and purity were determined using a NanoDrop spectrophotometer. Each tumor was homogenized with a disposable dispersing aggregate to avoid cross contamination between samples.

Protein Analysis with IPW: 1 mg of total tumor lysates were incubated with the chimeric EGFR antibody, cetuximab (ERBITUX; ImClone), which targets the extracellular domain of EGFR. The next day, the antibody conjugates were extracted using protein G-Sepharose beads and EGFR was eluted by incubation at 95° C. in loading buffer. The proteins were subsequently resolved by 8% polyacrylamide gel electrophoresis under reducing conditions and transferred to Immobilon-P membrane (Millipore, Bedford, Mass.). Western blotting was performed first with the anti-phosphotyrosine 4G10 antibody (Upstate, Lake Placid, N.Y.) to evaluate the phosphorylation status of EGFR. Next, the membrane is incubated with an anti-EGFR antibody (Agazie and Hayman, *Mol. Cell Biol.* 23:7875-7886, 2003) that recognizes the intracellular C-terminal domain of the receptor. Fluorescent secondary antibodies were used to develop the Western blots so that EGFR expression and phosphorylation can be quantified by the Odyssey Infrared Imaging System (LI-COR Biosciences, Lincoln, Nebr.). Mean EGFR expression of all samples was calculated. Tumors with EGFR expression above the mean were defined as high expressors.

RNA Analysis with RT-PCR and DNA Sequencing: Reverse transcription was carried out using a SuperScript Preamplification Kit (Life Technologies) on 1 μg of total RNA aliquots. PCR was performed using capillary LightCycler (Roche, Indianapolis, Ind.) with the following sets of EGFR primers.

```
Set 1:
                                         (SEQ ID NO: 5)
5'-GGCGAGTCGGGCTCTGGAGGAAAAG-3'
and (SEQ ID NO: 6)
5'-GGCCCTTCGCACTTCTTACACTTG-3'.
```

```
Set 2:
                                         (SEQ ID NO: 7)
5'-CCTGGGGATCGGCCTCTTCAT-3'
and (SEQ ID NO: 8)
5'-CACCCCGTAGCTCCAGACATCA-3'.
```

The Set 1 primer pair was designed to amplify the coding sequences from nucleotides 60 to 995 that cover the extracellular domain of EGFR (exon 1-8). The Set 2 primer pair was designed to amplify the coding sequences from nucleotides 1983 to 2706 that cover the intracellular tyrosine kinase domain of EGFR (exon 17-22). PCR was performed under the following conditions: denaturating 10 secs at 95° C., annealing 5 secs at 60° C. for Set 1 primers and at 50° C. for Set 2 primers, extension 30 secs at 72° C. A total of 45 and 37 cycles were performed respectively for Set 1 and 2 primer pair. The PCR end products were resolved by 2% agarose gel electrophoresis and isolated using Qiagen PCR Extraction Kit (QIAGEN Inc., Santa Clarita, Calif.). DNA sequencing was performed at the Sequencing Core Facility of the Stony Brook University Medical Center.

Immunohistochemistry and Histology: Tumor sections were deparaffinized, rehydrated and antigen retrieval was performed by microwave heating in sodium citric solution. After washing with PBS, the sections were treated with blocking serum (Vectastain ABC-AP kit, Vector Laboratories, Ca) and incubated with an anti-EGFR antibody (Cell Signaling, Beverly, Mass.) at 1:50 dilution overnight at 4° C. The tumor sections were subsequently washed with PBS and stained using the ABC-AP kit and the Vector Red alkaline phosphatase substrate solution (Vector Red, Vector Laboratories, CA). All matched H&E stained tumor sections were reviewed by a surgical pathologist (KRS) to confirm the diagnosis and determine the ratio of surface area occupied by the tumor to stroma. Histologic assessment was performed without knowledge of the molecular testing results and clinical data.

Statistics Analysis: Statistical analyses were performed using SPSS Statistics 16.0 (SPSS Inc., Chicago, Ill.). Comparison between pEGFR+ and pEGFR− group was performed using two samples t-test. We performed log transformation to normalize the distribution of EGFR expression for comparison. Chi square test was used to analyze the significance of the association between EGFR status and tumor characteristics.

Our results are presented below.

Example 2

EGFR Expression and Activation Analyses in HNSCC

Figure 1A:
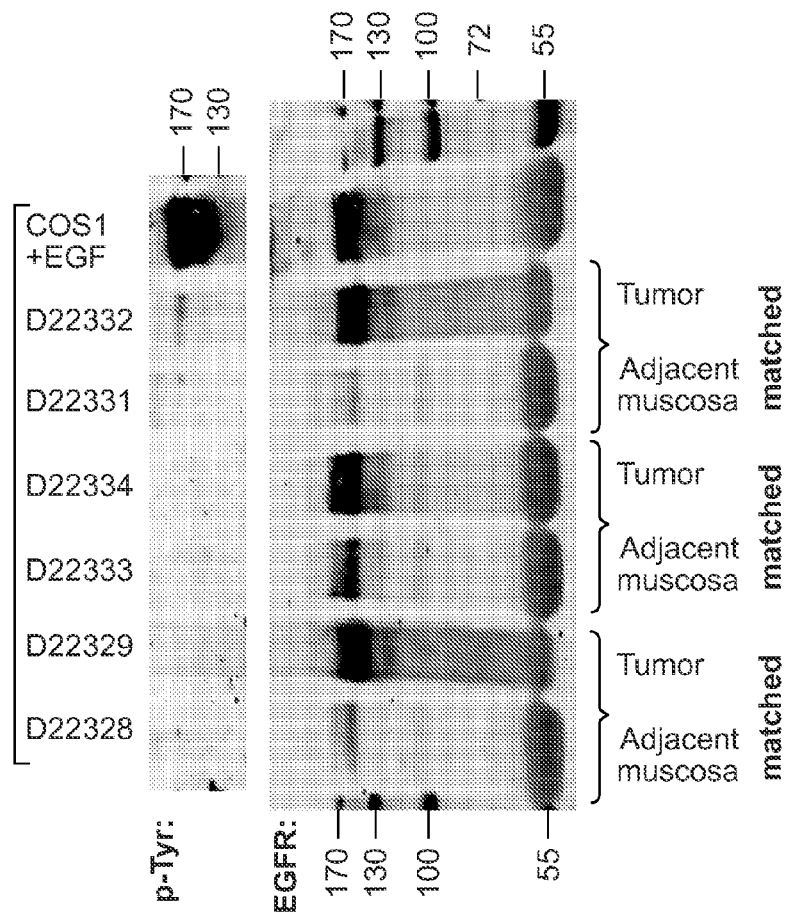
Figure 1D:
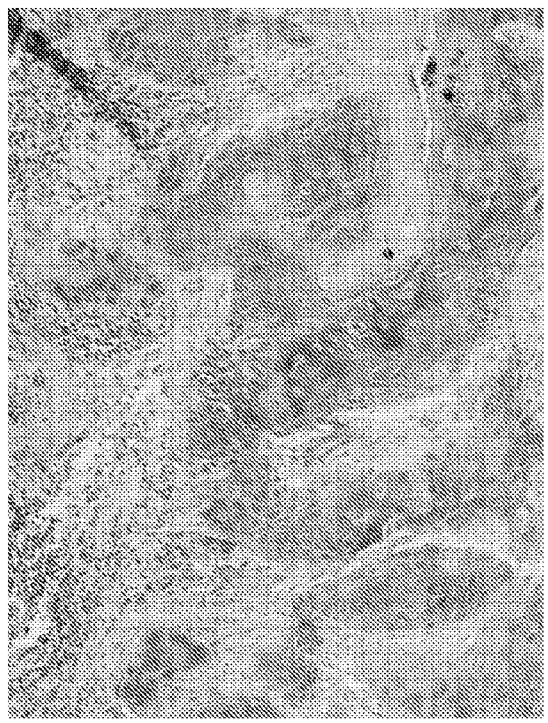
Figure 1C:
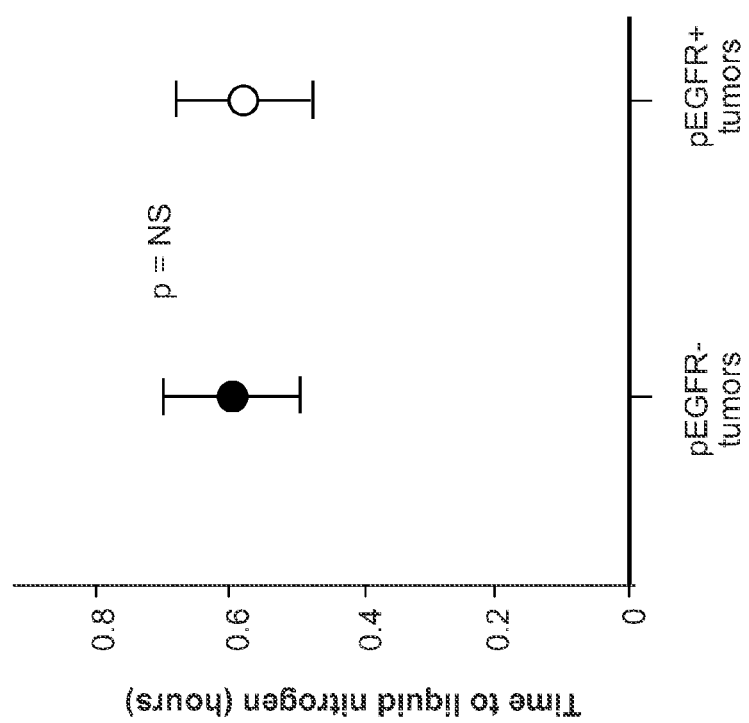

EGFR protein analysis was performed by IPW and IHC on 60 primary HNSCC. The IPW analysis surprisingly showed that only 40% (24/60) of HNSCC had tyrosine phosphorylated EGFR. As shown in FIG. 1, despite having similar level of EGFR expression among the three tumors (D22329, D22334 and D22332), only D22332 has detectable phosphorylated EGFR (FIG. 1A). While EGFR phosphorylation strongly correlated with its expression level (i.e. the higher the EGFR expression, the more likely the receptor is phosphorylated), there were tumors with equivalent amounts of EGFR that differed in their activation status (FIG. 1B). Nevertheless, it is clear from this data that tumors with low EGFR expression are unlikely to have activated EGFR. To evaluate the possibility that phosphorylation was lost during the processing of the tumors, we examined the difference in time taken from surgical excision of the tumor to liquid nitrogen storage between the phosphorylated and unphosphorylated tumors. There was no significant difference between their processing times. Mean processing time was 0.56±0.24 and 0.59±0.29 hours (p=0.67) for pEGFR+ (n=22) and pEGFR− (n=34) tumors respectively (FIG. 1C). Processing time data was missing for 4 cases. Thus, the detection of EGFR phosphorylation is not directly related to the processing time. One shortcoming of the IPW method is its inability to localize protein expression to a specific cell type, due to the heterogeneity of the homogenized lysates. Therefore, IHC was performed to confirm EGFR expression in the cancer cells. IHC also allow correlation of EGFR expression with morphologic evidence of tumor viability. As shown in FIG. 1D, IHC detected EGFR expression only in the carcinomas and no staining was seen when the primary antibodies were omitted (data not shown).

Example 3

Mutation Analysis of EGFR in HNSCC by RT-PCR

Figure 2B:
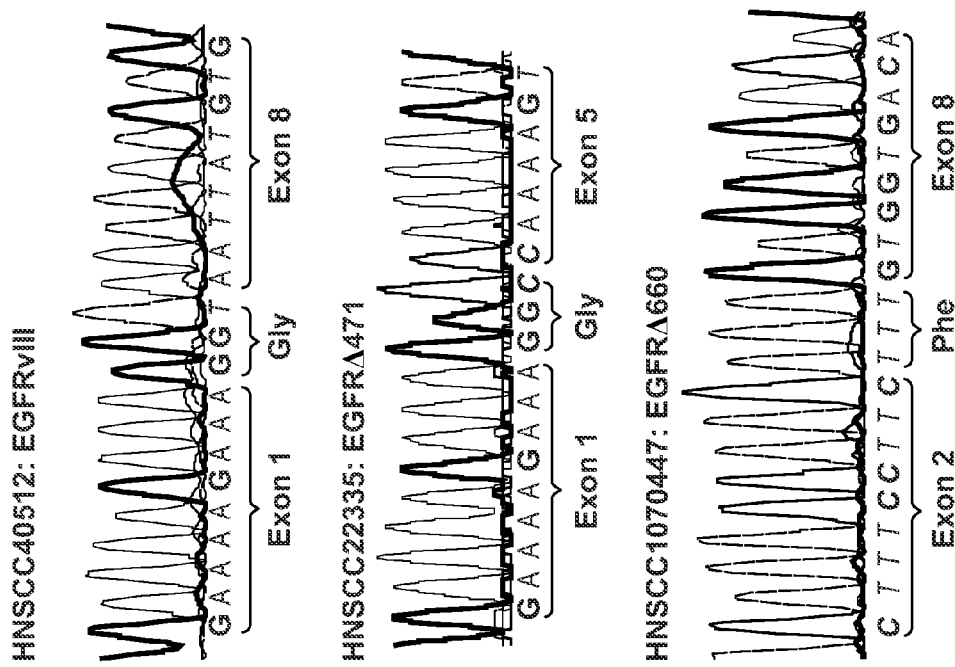
FIGS. 2A-2C show RNA analysis by RT-PCR. (A) RT-PCR screening of EGFR variants in a representative panel of primary HNSCC. FL-EGFR: full length EGFR. (B) DNA sequences of the exon 1-8 RT-PCR end products from three representative HNSCC. Top panel is DNA sequence representing EGFRvIII;(SEQ ID NO: 14); middle panel shows EGFRΔ471 (SEQ ID NO: 15) sequence and the bottom panel is EGFRΔ660 (SEQ ID NO: 16)sequence. All EGFR truncations were confirmed in both directions. (C) DNA sequences of the exon 17-22 RT-PCR end products from four representative HNSCC. The black arrow points to the missense mutation (C→T) in nucleotide 2197 of EGFR exon 19 of HNSCC1062007(SEQ ID NO: 17). The change in amino acid of this P733S mutation is illustrated by the amino acid sequence at the bottom. DNA sequences of the remaining three HNSCC (1061760, 1070032 and 1061699) are wild type(SEQ ID NO:18). EGFR kinase mutations were confirmed in both directions.
Figure 2A:
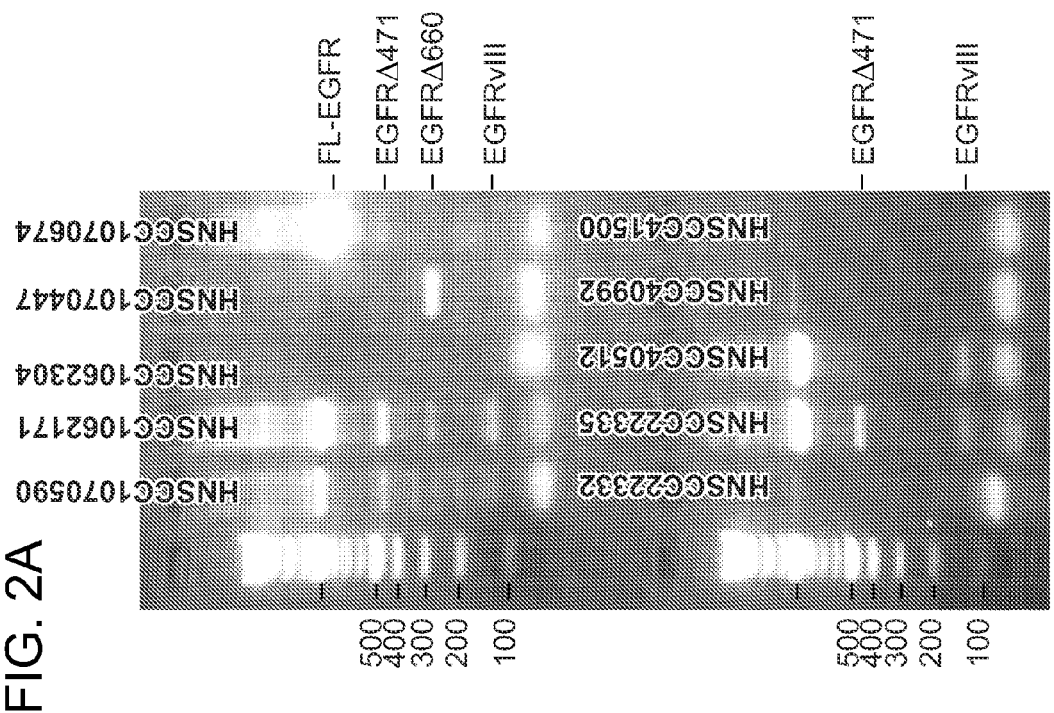

Since we used an EGFR antibody that binds the extracellular domain to pull down EGFR in the IPW method, truncated variants of EGFR that lack portions of the extracellular domain such as EGFRvIII might not be recognized with this assay. In addition, IHC will not be able to distinguish between the truncated and full length EGFR because the EGFR antibody for IHC binds the C-terminal of the receptor, which is present in both forms. To overcome this limitation, we used RT-PCR to screen for truncated EGFR in the 60 HNSCC. Like others (Sok et al., *Clin. Cancer Res.* 12:5064-5073, 2006), we found EGFRvIII in some HNSCC (FIG. 2). DNA sequencing of the RT-PCR end products confirms the identity (upper panel, FIG. 2B). Surprisingly, we also discovered two novel truncated variants of EGFR (FIG. 2A). Both variants have not been previously reported. The first variant, EGFRΔ471, carries an in-frame deletion from nucleotide 89 of exon 1 to nucleotide 559 of exon 4 (we may also refer to this truncation as Δ471). Most fascinating is the formation of a new codon (GGC) at the splice junction, which translates into a glycine residue (middle panel, FIG. 2B); this is similar to that seen in EGFRvIII. The second truncated variant, EGFRΔ660, has an in-frame deletion from nucleotide 237 of exon 2 to nucleotide 896 of exon 8 (we may also refer to this truncation as Δ660). Again, there is the formation of a new codon (TTT) at the splice junction, which translates into a phenylalanine residue (lower panel, FIG. 2B). We believe these two novel EGFR variants possess oncogenic potential just like EGFRvIII.

Figure 2C:
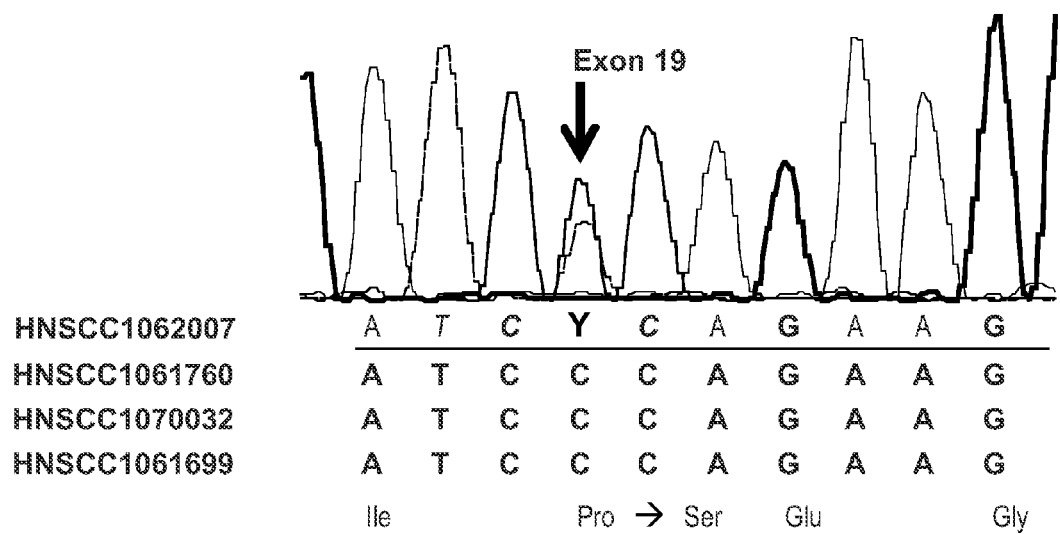

Next, to determine if any of the tumor samples had activating kinase mutations, we sequenced exon 17-22 of the EGFR tyrosine kinase domain. We found none of the known activating mutations in exon 18, 19, 20 and 21. Interestingly, in two of the samples, we identified two missense mutations. The first mutation is a change in nucleotide 2197 of exon 19, resulting in a change of the codon from CCA to TCA (FIG. 2C). This changes the encoded amino acid from proline to serine (P733S). Using the PolyPhen program that predicts functional effect of human non-synonymous SNPs, the P733S mutation is predicted to have probable functional consequences. This mutation brings closest contact with the Tyr 922 phosphorylation site (3.918 Å) and was identified in a T3N2 laryngeal tumor with high EGFR expression and truncated EGFR. The P733S mutation has only been described once previously in a synovial sarcoma (Bode et al., *Mod. Pathol.* 19:541-547, 2006). The second mutation is a change in nucleotide 2243 of exon 19, resulting in a change of the codon from AGA to ATA (data not shown). This changes the amino acid from arginine to isoleucine (R748I). However, the PolyPhen program predicts that the R748I mutation is likely benign. To our knowledge, this mutation has not been previously reported in any other tumors. Overall, the frequency of kinase mutations in our study population is low. This is consistent with the recent report that only 7% of HNSCC have kinase mutations (Hama et al., *Oncologist* 14:900-908, 2009). The mutations that we identified are different from the ones reported by these investigators. In addition, they did not find any extracellular mutations while we found two novel truncations in addition to EGFRvIII.

Example 4

Clinical Biological Correlates of EGFR Expression, Phosphorylation and Mutation in Combination Table I summarizes the clinical and pathological characteristics of our study population. The majority of the patients are caucasian male, less than 65, who smoked and/or drank. The majority of the tumors are located in the oropharynx, moderately differentiated with equal distribution of low and high tumor or nodal stage. These characteristics are similar to other study populations in North America (Grandis et al., *J. Natl. Cancer Inst.* 90:824-832, 1998; Ang et al., *Cancer Res.* 62:7350-7356, 2002). Of the 60 primary HNSCC, tumor stage was not addressed in the pathology report of 1 case and nodal staging was missing for 4 cases that did not include neck dissections. As shown in Table II, there were no significant relations between phosphorylation or high expression of EGFR alone with advanced tumor, nodal or overall stage. These results are consistent with what others have reported (Grandis et al., supra; Ang et al., supra; Hiraishi et al., supra). On the other hand, when HNSCC with either phosphorylated or truncated EGFR were analyzed in combination, a statistically significant association was found between those that are positive for either phosphorylated or truncated EGFR and higher tumor or nodal stage (Table II). In addition, there is a trend towards significant correlation between phosphorylated or truncated EGFR+ tumors and higher overall stage. To our surprise, we also noticed a significant association between truncated EGFR positivity alone and advanced tumor stage as well as overall stage. However, the number of low stage tumors with truncated EGFR is very small and therefore this can easily skew the chi square analysis towards significance. We also correlated EGFR status to age, sex, risk factors such as smoking and alcohol use, histologic features such as differentiation and invasion, but did not find any significant association (data not shown). Nevertheless, we found that patients with ΔEGFR+ HNSCC are significantly younger with mean age of 52.8±9.0 years than ΔEGFR− patients (mean age=59.6±12.5 years, p=0.02). Overall, these results suggest that HNSCC with either truncated or activated EGFR tend to have higher tumor and nodal stage.

Discussion: Ample data over the last 20 years strongly support an important role of EGFR and its ligands in the development and progression of HNSCC. Overexpression of EGFR has been reported in up to 80% of HNSCC (Quon et al., *Head Neck*, 23:147-159, 2001); EGFR mRNA and protein levels are also increased in dysplastic lesions and histologically normal mucosa from HNSCC patients (Ford and Grandis, *Head Neck*, 25:67-73, 2003). Studies further exploring the prognostic value of EGFR in HNSCC began to emerge in the late 90s. Quantitative differences in EGFR protein levels are reliable predictors of adverse outcome in head and neck cancer patients (Grandis et al., *J. Natl. Cancer Inst.* 90:824-832, 1998; Ang et al., *Cancer Res.* 62:7350-7356, 2002; Etienne et al., *Br. J. Cancer* 79:1865-1869, 1999). With these data, strategies to block EGFR activity were developed. EGFR targeting agents are now in clinical trials for HNSCC. Despite the mountain of evidence suggesting the importance of EGFR in HNSCC, the results of various clinical trials testing different EGFR inhibitors are not as dramatic as one would expect. Phase II studies testing the efficacy of EGFR inhibitors such as gefitinib (IRESSA), erlotinib (TARCEVA) and cetuximab (ERBITUX) in treating recurrent or metastatic HNSCC yield a response rate of 5-10% (Cohen et al., *J. Clin. Oncol.* 21:1980-1987, 2003; Soulieres et al., *J. Clin. Oncol.* 22:77-85, 2004; Baselga et al., *J. Clin. Oncol.* 23:5568-5577, 2005). While the phase III randomized clinical trial showed that ERBITUX improved the local regional control and significantly prolonged the progression-free survival of patients with advanced stage HNSCC, the overall survival at 3 years only improved by 10% (Bonner et al., *N. Engl. J. Med.* 354:567-578, 2006). Aside from the limited therapeutic benefit of EGFR inhibitors, another puzzling observation noted in these studies was the lack of correlation between EGFR expression and disease stage (Grandis et al., supra; Ang et al., supra); this suggests that other factors may contribute to disease aggressiveness. A recent study found that 42% of HNSCC expresses the EGFR truncation mutant, EGFRvIII (Sok et al., *Clin. Cancer Res.* 12:5064-5073, 2006). EGFRvIII is a deletion mutant of the EGFR gene that was' first discovered in glioblastomas (Pedersen et al., *Ann. Oncol.* 12:745-760, 2001). This mutant contains an in-frame deletion from exon 2-7 (Δ801) and encodes a truncated receptor that is constitutively active, but lacks the majority of the extracellular domain. Evidence that cancer cells with EGFRvIII expression were not as sensitive to ERBITUX or TARCEVA is now emerging in different reports (Sok et al., *Clin. Cancer Res.* 12:5064-5073, 2006). Thus, truncated forms of EGFR may be another important aspect of EGFR in HNSCC.

In the study described above, we investigated whether EGFR status and disease staging correlates when the different aspects of the receptor are evaluated in combination. Several interesting yet unexpected results surfaced from our analyses. The first is that HNSCC with equivalent amount of EGFR do not necessarily possess similar receptor activity level. Of the 60 HNSCC, only 40% have phosphorylated EGFR. It is conceivable that only those tumors with activated EGFR respond to EGFR inhibitors. While not all EGFR expressing tumors have phosphorylated EGFR, the higher the expression, the more likely the EGFR is active. Our data is consistent with previous reports that both high EGFR expression and phosphorylated EGFR correlated with worse disease free survival (Grandis et al., supra; Ang et al., supra). However, phosphorylated EGFR alone does not predict advanced stage disease. Thus, we examined other aspects of the receptor and searched for EGFR mutations. Like others, we found EGFRvIII in 23% HNSCC. Surprisingly, we also discovered two novel EGFR truncations, EGFRΔ471 and Δ660. To our knowledge, these mutants have not been previously described in primary tumors; both contain in-frame deletions of the EGFR extracellular domain, similar to EGFRvIII. When analyzed in combination, truncated EGFR synergizes with phosphorylated EGFR in the correlation with advanced stage disease. HNSCC with either truncated forms of EGFR or activated full length EGFR tend to be of higher tumor and nodal stage. We excluded the possibility of kinase mutants contributing to the correlation, as only two samples carry kinase mutations. Therefore, activated and truncated EGFR together might represent biomarkers for aggressive HNSCC. Another interesting finding from this study is the discovery of three potentially significant EGFR mutations: two novel extracellular mutants and the P733S missense kinase mutation. While other EGFR deletion mutants have been identified in glioblastomas (Frederick et al., *Cancer Res.* 60:1383-1387, 2000), the ones that we discovered in HNSCC were distinctly different. They closely resemble EGFRvIII and therefore might possess oncogenic potential. A recent report suggested that genomic deletions occur at breakpoints around Alu repeat elements in EGFR introns 1 and 7 could be the potential mechanism of EGFRvIII synthesis (Frederick et al., *Neuro. Oncol.* 2:159-163, 2000). Given this finding, we postulate that EGFRΔ471 and 660 production may be the result of genomic alterations. While EGFR kinase mutations are rare in HNSCC, they do exist in a low percentage of tumors as demonstrated in this and other studies (Hama et al., *Oncologist* 14:900-908, 2009; Loeffler-Ragg et al., *Eur. J. Cancer* 42:109-111, 2006; Lee et al., *Clin. Cancer Res.* 11:2879-2882, 2005). Analyses of multiple sequence alignments and protein 3D-structures by the PolyPhen program predict with high confidence that the P733S mutation affects the protein structure and function. Further biochemical characterization of these mutations is needed to define their functional significance.

It has become increasingly clear from this and other studies that even tumors with the same histologic diagnoses are not the same in terms of their molecular profile. Some of these differences may dictate patients' response to molecular target therapy. For instance, only about 10% of patients with non-small cell lung cancer have activating mutations in the EGFR tyrosine kinase domain; these patients demonstrated dramatic response to gefitinib (Lynch et al., *N. Engl. J. Med.* 350:2129-2139, 2004). As shown in our study, not all EGFR expressing HNSCC are the same. Thus, there has been increasing emphasis on the application of molecular biomarkers to further classify cancer of the same histologic diagnosis. To understand the target better, we used various methods to analyze EGFR in HNSCC. It is apparent that each technique offers an advantage on examining a certain aspect of the receptor. Together, the results provided a more in-depth molecular characterization of EGFR in the tumor. The value of this approach can be seen when more accurate clinical biological correlation was observed with different EGFR status evaluated in combination. Although many translational studies used IHC to analyze EGFR expression, protein expression is only one aspect of the receptor status; by itself, expression may not always tell the whole story.

While many HNSCC express a high level of EGFR, not all high EGFR expressing HNSCC have the activated receptor. In addition, some HNSCC express truncated forms of EGFR. The combination of truncated and activated EGFR is associated with advanced tumor and nodal stage; these two aspects of EGFR may predict patients' response to EGFR targeting therapy. Patients with tumors carrying activated EGFR may respond better to ERBITUX than those with truncated EGFR. Efforts are currently ongoing to further characterize the oncogenic potential of the two novel EGFR truncations.

Example 5

EGFR Expression and Activation Analyses in Neuroblastic Tumors and Cell Lines

In other studies, we obtained 62 neuroblastic tumors from the Children's Oncology Group tissue bank. Frozen tumors were homogenized and centrifuged. The supernatant was used for protein and RNA analyses. EGFR phosphorylation and expression were analyzed by immunoprecipitation followed by Western blot analysis. EGFR expression was quantified using an Infrared Imaging System that detected fluorescence emitted by the secondary antibodies. Tumor cDNA were screened for EGFR mutations. We used primers to exon 1/8 and exon 17/22 to screen for truncation and activating mutations. PCR products were sequenced to confirm their identities.

Of the 62 tumors, 64% expressed full length EGFR. Their mean level of expression (x=2.83±1.28) was 40% less than that of head and neck squamous cell tumors (x=4.65±1.44, n=43). None had phosphorylated EGFR. No activating mutations were found. However, 34% expressed truncated forms of EGFR. Six expressed EGFRvIII. The other 15 expressed novel truncations, EGFRΔ471 (as described above; a deletion from nucleotide 89 of exon 1 to nucleotide 559 of exon 4) and Δ768 (a deletion from nucleotide 102 of exon 2 to 869 of exon 7). We also found EGFRΔ768 expression in one of five NBL cell lines.

Example 6

EGFR Expression and Activation Analyses in Neuroblastic Tumors

To study EGFR in NBL, we obtained IRB approval and made an application to the Children's Oncology Group (COG) tissue bank for frozen primary neuroblastoma. We received a total of 62 tumors. These tumors are not specimen procured in conjunction with any COG NBL clinical trials. Instead, they were procured locally at various COG institutions outside of a therapeutic NBL trial. The tumors were provided to us as materials for this pilot study. Thus, only limited clinical data were available. To analyze EGFR, we prepared total RNA and cDNA from the homogenized tumors. Using RT-PCR, we screened the 62 samples for EGFR mutations.

As described above, while we did not find any activating kinase mutations in these tumors, we surprisingly discovered that 32% (20/62) expressed truncated forms of EGFR. RT-PCR analysis showed that 14 tumors expressed a novel EGFR truncation, whereas 6 expressed the EGFRvIII variant. RT-PCR analysis on a panel of representative neuroblastoma that express the EGFR truncation mutants is shown in FIGS. 6A and 6B. NBL 9374 expressed EGFRvIII as confirmed by DNA sequencing (FIGS. 6A and 6D), while NBL 7853 and 9376 expressed an EGFR truncation mutant that was slightly larger than EGFRvIII as indicated by the 167 bp band in (FIG. 6B). DNA sequencing confirmed that the novel EGFR truncation had an in-frame deletion from nucleotide 102 of exon 2 to nucleotide 869 of exon 7 (Δ768) as shown in FIG. 4E. This Δ768 deletion resulted in a transcript coding for 11 more amino acids than are in the amino acid sequence of EGFRvIII. Next, we search for truncated EGFR in 5 different neuroblastoma cell lines (NBLs). To our surprise, we found the same novel variant, EGFRΔ768, in the NBL cell line, BE2M17. cDNAs from NBL 9374 and 7853 were gel purified and used as positive controls in this experiment (FIG. 6C). The identity of all PCR products was confirmed by DNA sequencing.

FIG. 7: Functional Analysis of EGFRΔ768

To further characterize the function of EGFRΔ768, we first obtained a wild type (WT) EGFR-GFP expression vector with neomycin selection cassette (courtesy of Dr. Dafna Bar-Sagi). Then, we subcloned the novel extracellular deletion mutant Δ768 into this vector. We confirmed the identity of EGFRΔ768-GFP vector by DNA sequencing. Next, we transfected both GFP tagged WT-EGFR and EGFRΔ768 into NIH 3T3 cells. We used 3T3 cells for our initial analysis because these cells express trivial amount of endogenous WT-EGFR. Surprisingly, western blot analysis showed a much more intense phosphorylation signal from EGFRΔ768 in the absence of ligand than was observed for WT-EGFR in the absence of ligand (FIG. 7A). This implied that EGFRΔ768 was constitutively active. Even though a large portion of the extracellular domain of EGFR was deleted in EGFRΔ768, we found that the monoclonal antibody, cetuximab (Erbitux) still bounds the EGFRΔ768 polypeptide and was able to immunoprecipitate both WT-EGFR and EGFRΔ768 (FIG. 7A). This was not unexpected as Erbitux is known to bind domain III of EGFR (25), which is intact in both EGFRvIII (8) and EGFRΔ768.

We then asked whether there were biochemical differences between EGFRΔ768 and EGFRvIII. First, we subcloned EGFRvIII deletion into the GFP-tagged WT-EGFR vector. Then, we transfected GFP-tagged EGFRvIII and EGFRΔ768 vectors separately into the neuroblastoma cell line, SY5Y. We observed a high transfection efficiency in NBL cells using standard lipotransfection method (FIGS. 7B and 7E). Then, we prepared RNA and protein lysates from the transfected cells. We confirmed the identity of the lysates by RT-PCR (FIG. 7C). Next, we evaluated the phosphorylation status of both mutants. Because SY5Y cells expressed endogenous WT-EGFR (21, 22), we used anti-GFP antibody to immunoprecipitate the mutant EGFR polypeptides. As shown in FIG. 7D, EGFRΔ768 was autophosphorylated at higher level than was EGFRvIII (about a 40% difference). Both mutants were more active than WT-EGFR when overexpressed. These results suggested that in spite of the similarities in animo acid sequence, EGFRΔ768 may be functionally distinct from EGFRvIII.

Example 8

Effect of the EGFR Tyrosine Kinase Inhibitor on EGFRΔ768

Figure 8A:
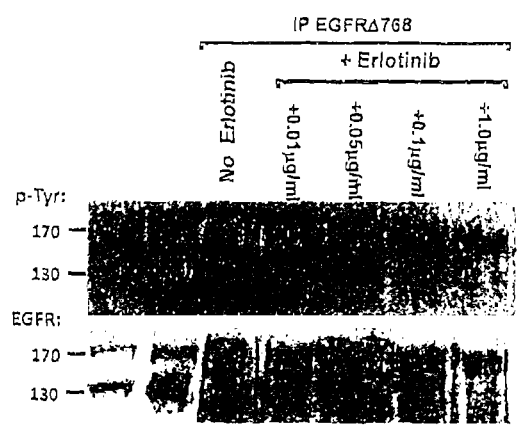
FIG. 8A shows the results of an analysis of the phosphylation status of EGFRΔ768 in cells that had been exposed to increasing concentrations of the EGFR tyrosine kinase inhibitor, erlotinib.
Figure 8B:
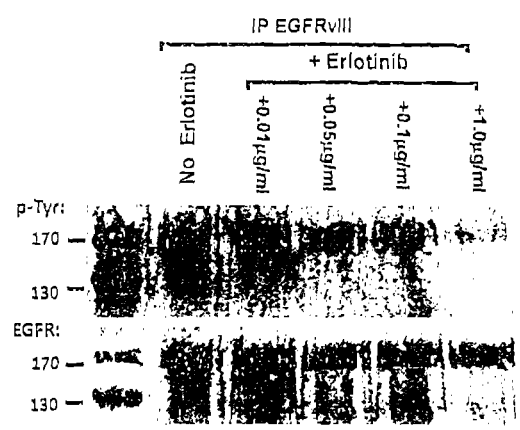
FIG. 8B shows the results of an analysis of the phosphylation status of EGFRvIII in cells that had been exposed to increasing concentrations of the EGFR tyrosine kinase inhibitor, erlotinib.

We then asked if the EGFRΔ768 mutation altered the sensitivity of EGFR to the EGFR tyrosine kinase inhibitor, erlotinib. We compared the levels of phosphorylated EGFR in EGFRΔ768 and EGFRvIII that had been exposed to increasing concentrations of ertinolab. The results of this experiment for EGFRΔ768 and EGFRvIII are shown in FIGS. 8A and 8B, respectively. We found that phosphorylation of EGFRΔ768 appeared more resistant to ertinolib relative to EGFRvIII.

Figure 9:
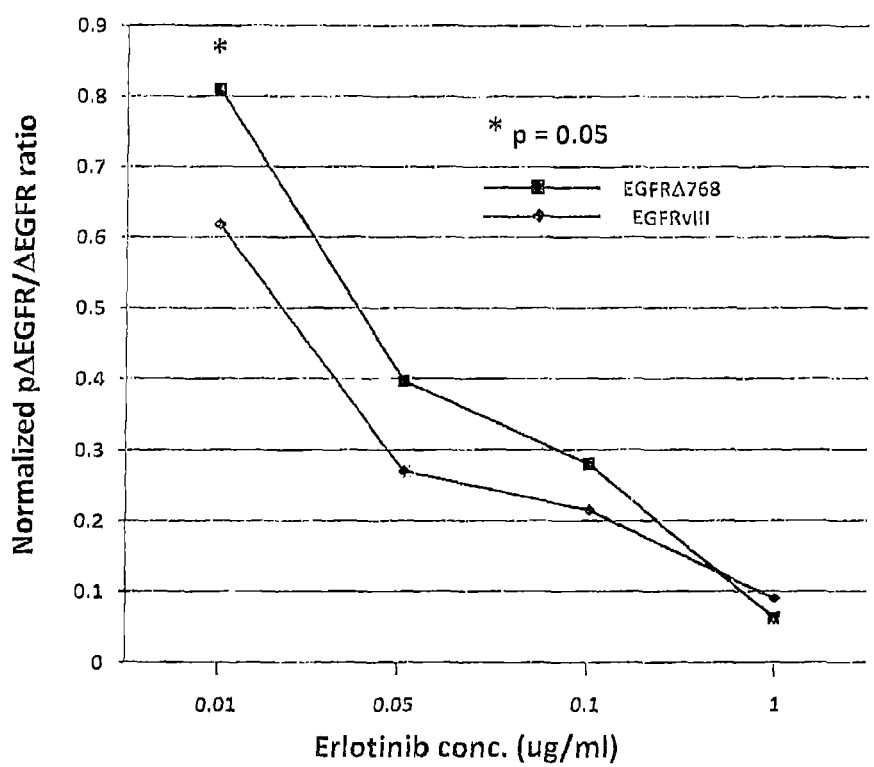
FIG. 9 is a graph depicting a dose-response analysis of the effect of the EGFR tyrosine kinase inhibitor, erlotinib, on the phosphorylation status of EGFRΔ768 and EGFRvIII.

This experiment was repeated three times. In order to generate dose-response curves, phosphorylated EGFRΔ768 and EGFRvIII were quantified and normalized to the total EGFRΔ768 and EGFRvIII. The ratio of pEGFRΔ768/vIII to total EGFRΔ768/vIII in the untreated cell lysate was normalized to 1. The degree of EGFRΔ768/vIII inhibition was expressed as percent reduction from the normalized ratio of 1 in the untreated cells. As shown in FIG. 9, autophosphorylation of EGFRΔ768 was consistently less sensitive to ertinolib at all but the highest concentration tested. At the lowest concentration (0.01 ug/ml) this difference was statistically significant (p=0.05).

A number of embodiments of the invention have been described. Nevertheless, it will be understood that various modifications may be made without departing from the spirit and scope of the invention.

What is claimed is:

1. A purified antibody that specifically binds to an epitope in the extracellular domain of EGFRΔ768.

2. The antibody of claim 1, wherein the epitope is encoded by a 20 base pair nucleic acid sequence spanning the splice junction between nucleotide 102 of exon 2 and nucleotide 869 of exon 7.

3. The antibody of claim 2, wherein the nucleic acid sequence comprises the sequence 5'TGCCAAGGCACCT-GCGTG3' (SEQ ID NO: 13).

4. A kit comprising a measured amount of the antibody of claim 1.

* * * * *

UNITED STATES PATENT AND TRADEMARK OFFICE
CERTIFICATE OF CORRECTION

| | | |
|---|---|---|
| PATENT NO. | : 8,962,808 B2 | Page 1 of 1 |
| APPLICATION NO. | : 13/696291 | |
| DATED | : February 24, 2015 | |
| INVENTOR(S) | : Edward L. Chan et al. | |

It is certified that error appears in the above-identified patent and that said Letters Patent is hereby corrected as shown below:

In the Specification

The text under the heading GOVERNMENT SUPPORT at column 1, line 16- line 19 "This invention was made with government support awarded by the National Institute of Health under grant number 1R21CA133652-01A2. The government has certain rights in the invention."

should be replaced with

--This invention was made with government support under grant number CA133642 awarded by the National Institutes of Health. The government has certain rights in the invention.--

Signed and Sealed this
Seventh Day of July, 2015

Michelle K. Lee
*Director of the United States Patent and Trademark Office*

SEQUENCE LISTING

<160> NUMBER OF SEQ ID NOS: 20

<210> SEQ ID NO 1
<211> LENGTH: 954
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

```
Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gly
             20                  25                  30

Gln Thr Cys Val Lys Lys Cys Pro Arg Asn Tyr Val Thr Asp His
         35                  40                  45

Gly Ser Cys Val Arg Ala Cys Gly Ala Asp Ser Tyr Glu Met Glu Glu
     50                  55                  60

Asp Gly Val Arg Lys Cys Lys Lys Cys Glu Gly Pro Cys Arg Lys Val
 65                  70                  75                  80

Cys Asn Gly Ile Gly Ile Gly Glu Phe Lys Asp Ser Leu Ser Ile Asn
                 85                  90                  95

Ala Thr Asn Ile Lys His Phe Lys Asn Cys Thr Ser Ile Ser Gly Asp
            100                 105                 110

Leu His Ile Leu Pro Val Ala Phe Arg Gly Asp Ser Phe Thr His Thr
        115                 120                 125

Pro Pro Leu Asp Pro Gln Glu Leu Asp Ile Leu Lys Thr Val Lys Glu
    130                 135                 140

Ile Thr Gly Phe Leu Leu Ile Gln Ala Trp Pro Glu Asn Arg Thr Asp
145                 150                 155                 160

Leu His Ala Phe Glu Asn Leu Glu Ile Ile Arg Gly Arg Thr Lys Gln
                165                 170                 175

His Gly Gln Phe Ser Leu Ala Val Val Ser Leu Asn Ile Thr Ser Leu
            180                 185                 190

Gly Leu Arg Ser Leu Lys Glu Ile Ser Asp Gly Asp Val Ile Ile Ser
        195                 200                 205

Gly Asn Lys Asn Leu Cys Tyr Ala Asn Thr Ile Asn Trp Lys Lys Leu
    210                 215                 220

Phe Gly Thr Ser Gly Gln Lys Thr Lys Ile Ile Ser Asn Arg Gly Glu
225                 230                 235                 240

Asn Ser Cys Lys Ala Thr Gly Gln Val Cys His Ala Leu Cys Ser Pro
                245                 250                 255

Glu Gly Cys Trp Gly Pro Glu Pro Arg Asp Cys Val Ser Cys Arg Asn
            260                 265                 270

Val Ser Arg Gly Arg Glu Cys Val Asp Lys Cys Asn Leu Leu Glu Gly
        275                 280                 285

Glu Pro Arg Glu Phe Val Glu Asn Ser Glu Cys Ile Gln Cys His Pro
    290                 295                 300

Glu Cys Leu Pro Gln Ala Met Asn Ile Thr Cys Thr Gly Arg Gly Pro
305                 310                 315                 320

Asp Asn Cys Ile Gln Cys Ala His Tyr Ile Asp Gly Pro His Cys Val
                325                 330                 335

Lys Thr Cys Pro Ala Gly Val Met Gly Glu Asn Asn Thr Leu Val Trp
            340                 345                 350
```

```
Lys Tyr Ala Asp Ala Gly His Val Cys His Leu Cys His Pro Asn Cys
            355                 360                 365

Thr Tyr Gly Cys Thr Gly Pro Gly Leu Glu Gly Cys Pro Thr Asn Gly
370                 375                 380

Pro Lys Ile Pro Ser Ile Ala Thr Gly Met Val Gly Ala Leu Leu Leu
385                 390                 395                 400

Leu Leu Val Val Ala Leu Gly Ile Gly Leu Phe Met Arg Arg Arg His
                405                 410                 415

Ile Val Arg Lys Arg Thr Leu Arg Arg Leu Leu Gln Glu Arg Glu Leu
            420                 425                 430

Val Glu Pro Leu Thr Pro Ser Gly Glu Ala Pro Asn Gln Ala Leu Leu
            435                 440                 445

Arg Ile Leu Lys Glu Thr Glu Phe Lys Lys Ile Lys Val Leu Gly Ser
450                 455                 460

Gly Ala Phe Gly Thr Val Tyr Lys Gly Leu Trp Ile Pro Glu Gly Glu
465                 470                 475                 480

Lys Val Lys Ile Pro Val Ala Ile Lys Glu Leu Arg Glu Ala Thr Ser
                485                 490                 495

Pro Lys Ala Asn Lys Glu Ile Leu Asp Glu Ala Tyr Val Met Ala Ser
            500                 505                 510

Val Asp Asn Pro His Val Cys Arg Leu Leu Gly Ile Cys Leu Thr Ser
            515                 520                 525

Thr Val Gln Leu Ile Thr Gln Leu Met Pro Phe Gly Cys Leu Leu Asp
            530                 535                 540

Tyr Val Arg Glu His Lys Asp Asn Ile Gly Ser Gln Tyr Leu Leu Asn
545                 550                 555                 560

Trp Cys Val Gln Ile Ala Lys Gly Met Asn Tyr Leu Glu Asp Arg Arg
                565                 570                 575

Leu Val His Arg Asp Leu Ala Ala Arg Asn Val Leu Val Lys Thr Pro
            580                 585                 590

Gln His Val Lys Ile Thr Asp Phe Gly Leu Ala Lys Leu Leu Gly Ala
            595                 600                 605

Glu Glu Lys Glu Tyr His Ala Glu Gly Gly Lys Val Pro Ile Lys Trp
610                 615                 620

Met Ala Leu Glu Ser Ile Leu His Arg Ile Tyr Thr His Gln Ser Asp
625                 630                 635                 640

Val Trp Ser Tyr Gly Val Thr Val Trp Glu Leu Met Thr Phe Gly Ser
                645                 650                 655

Lys Pro Tyr Asp Gly Ile Pro Ala Ser Glu Ile Ser Ser Ile Leu Glu
            660                 665                 670

Lys Gly Glu Arg Leu Pro Gln Pro Pro Ile Cys Thr Ile Asp Val Tyr
            675                 680                 685

Met Ile Met Val Lys Cys Trp Met Ile Asp Ala Asp Ser Arg Pro Lys
690                 695                 700

Phe Arg Glu Leu Ile Ile Glu Phe Ser Lys Met Ala Arg Asp Pro Gln
705                 710                 715                 720

Arg Tyr Leu Val Ile Gln Gly Asp Glu Arg Met His Leu Pro Ser Pro
                725                 730                 735

Thr Asp Ser Asn Phe Tyr Arg Ala Leu Met Asp Glu Glu Asp Met Asp
            740                 745                 750

Asp Val Val Asp Ala Asp Glu Tyr Leu Ile Pro Gln Gln Gly Phe Phe
            755                 760                 765

Ser Ser Pro Ser Thr Ser Arg Thr Pro Leu Leu Ser Ser Leu Ser Ala
```

```
                     770                 775                 780
Thr Ser Asn Asn Ser Thr Val Ala Cys Ile Asp Arg Asn Gly Leu Gln
785                 790                 795                 800

Ser Cys Pro Ile Lys Glu Asp Ser Phe Leu Gln Arg Tyr Ser Ser Asp
                805                 810                 815

Pro Thr Gly Ala Leu Thr Glu Asp Ser Ile Asp Asp Thr Phe Leu Pro
            820                 825                 830

Val Pro Glu Tyr Ile Asn Gln Ser Val Pro Lys Arg Pro Ala Gly Ser
        835                 840                 845

Val Gln Asn Pro Val Tyr His Asn Gln Pro Leu Asn Pro Ala Pro Ser
    850                 855                 860

Arg Asp Pro His Tyr Gln Asp Pro His Ser Thr Ala Val Gly Asn Pro
865                 870                 875                 880

Glu Tyr Leu Asn Thr Val Gln Pro Thr Cys Val Asn Ser Thr Phe Asp
                885                 890                 895

Ser Pro Ala His Trp Ala Gln Lys Gly Ser His Gln Ile Ser Leu Asp
                900                 905                 910

Asn Pro Asp Tyr Gln Gln Asp Phe Phe Pro Lys Glu Ala Lys Pro Asn
                915                 920                 925

Gly Ile Phe Lys Gly Ser Thr Ala Glu Asn Ala Glu Tyr Leu Arg Val
                930                 935                 940

Ala Pro Gln Ser Ser Glu Phe Ile Gly Ala
945                 950

<210> SEQ ID NO 2
<211> LENGTH: 1053
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Gln Lys
                20                  25                  30

Cys Asp Pro Ser Cys Pro Asn Gly Ser Cys Trp Gly Ala Gly Glu Glu
            35                  40                  45

Asn Cys Gln Lys Leu Thr Lys Ile Ile Cys Ala Gln Gln Cys Ser Gly
        50                  55                  60

Arg Cys Arg Gly Lys Ser Pro Ser Asp Cys Cys His Asn Gln Cys Ala
65                  70                  75                  80

Ala Gly Cys Thr Gly Pro Arg Glu Ser Asp Cys Leu Val Cys Arg Lys
                85                  90                  95

Phe Arg Asp Glu Ala Thr Cys Lys Asp Thr Cys Pro Pro Leu Met Leu
                100                 105                 110

Tyr Asn Pro Thr Thr Tyr Gln Met Asp Val Asn Pro Glu Gly Lys Tyr
            115                 120                 125

Ser Phe Gly Ala Thr Cys Val Lys Lys Cys Pro Arg Asn Tyr Val Val
        130                 135                 140

Thr Asp His Gly Ser Cys Val Arg Ala Cys Gly Ala Asp Ser Tyr Glu
145                 150                 155                 160

Met Glu Glu Asp Gly Val Arg Lys Cys Lys Lys Cys Glu Gly Pro Cys
                165                 170                 175
```

```
Arg Lys Val Cys Asn Gly Ile Gly Ile Gly Glu Phe Lys Asp Ser Leu
            180                 185                 190

Ser Ile Asn Ala Thr Asn Ile Lys His Phe Lys Asn Cys Thr Ser Ile
            195                 200                 205

Ser Gly Asp Leu His Ile Leu Pro Val Ala Phe Arg Gly Asp Ser Phe
            210                 215                 220

Thr His Thr Pro Pro Leu Asp Pro Gln Glu Leu Asp Ile Leu Lys Thr
225                 230                 235                 240

Val Lys Glu Ile Thr Gly Phe Leu Leu Ile Gln Ala Trp Pro Glu Asn
                245                 250                 255

Arg Thr Asp Leu His Ala Phe Glu Asn Leu Glu Ile Ile Arg Gly Arg
            260                 265                 270

Thr Lys Gln His Gly Gln Phe Ser Leu Ala Val Val Ser Leu Asn Ile
        275                 280                 285

Thr Ser Leu Gly Leu Arg Ser Leu Lys Glu Ile Ser Asp Gly Asp Val
        290                 295                 300

Ile Ile Ser Gly Asn Lys Asn Leu Cys Tyr Ala Asn Thr Ile Asn Trp
305                 310                 315                 320

Lys Lys Leu Phe Gly Thr Ser Gly Gln Lys Thr Lys Ile Ile Ser Asn
                325                 330                 335

Arg Gly Glu Asn Ser Cys Lys Ala Thr Gly Gln Val Cys His Ala Leu
            340                 345                 350

Cys Ser Pro Glu Gly Cys Trp Gly Pro Glu Pro Arg Asp Cys Val Ser
        355                 360                 365

Cys Arg Asn Val Ser Arg Gly Arg Glu Cys Val Asp Lys Cys Asn Leu
        370                 375                 380

Leu Glu Gly Glu Pro Arg Glu Phe Val Glu Asn Ser Glu Cys Ile Gln
385                 390                 395                 400

Cys His Pro Glu Cys Leu Pro Gln Ala Met Asn Ile Thr Cys Thr Gly
                405                 410                 415

Arg Gly Pro Asp Asn Cys Ile Gln Cys Ala His Tyr Ile Asp Gly Pro
            420                 425                 430

His Cys Val Lys Thr Cys Pro Ala Gly Val Met Gly Glu Asn Asn Thr
        435                 440                 445

Leu Val Trp Lys Tyr Ala Asp Ala Gly His Val Cys His Leu Cys His
        450                 455                 460

Pro Asn Cys Thr Tyr Gly Cys Thr Gly Pro Gly Leu Glu Gly Cys Pro
465                 470                 475                 480

Thr Asn Gly Pro Lys Ile Pro Ser Ile Ala Thr Gly Met Val Gly Ala
                485                 490                 495

Leu Leu Leu Leu Leu Val Val Ala Leu Gly Ile Gly Leu Phe Met Arg
            500                 505                 510

Arg Arg His Ile Val Arg Lys Arg Thr Leu Arg Arg Leu Leu Gln Glu
        515                 520                 525

Arg Glu Leu Val Glu Pro Leu Thr Pro Ser Gly Glu Ala Pro Asn Gln
        530                 535                 540

Ala Leu Leu Arg Ile Leu Lys Glu Thr Glu Phe Lys Lys Ile Lys Val
545                 550                 555                 560

Leu Gly Ser Gly Ala Phe Gly Thr Val Tyr Lys Gly Leu Trp Ile Pro
                565                 570                 575

Glu Gly Glu Lys Val Lys Ile Pro Val Ala Ile Lys Glu Leu Arg Glu
            580                 585                 590

Ala Thr Ser Pro Lys Ala Asn Lys Glu Ile Leu Asp Glu Ala Tyr Val
```

```
                595                 600                 605
Met Ala Ser Val Asp Asn Pro His Val Cys Arg Leu Leu Gly Ile Cys
610                 615                 620

Leu Thr Ser Thr Val Gln Leu Ile Thr Gln Leu Met Pro Phe Gly Cys
625                 630                 635                 640

Leu Leu Asp Tyr Val Arg Glu His Lys Asp Asn Ile Gly Ser Gln Tyr
                645                 650                 655

Leu Leu Asn Trp Cys Val Gln Ile Ala Lys Gly Met Asn Tyr Leu Glu
                660                 665                 670

Asp Arg Arg Leu Val His Arg Asp Leu Ala Ala Arg Asn Val Leu Val
                675                 680                 685

Lys Thr Pro Gln His Val Lys Ile Thr Asp Phe Gly Leu Ala Lys Leu
690                 695                 700

Leu Gly Ala Glu Glu Lys Glu Tyr His Ala Glu Gly Gly Lys Val Pro
705                 710                 715                 720

Ile Lys Trp Met Ala Leu Glu Ser Ile Leu His Arg Ile Tyr Thr His
                725                 730                 735

Gln Ser Asp Val Trp Ser Tyr Gly Val Thr Val Trp Glu Leu Met Thr
                740                 745                 750

Phe Gly Ser Lys Pro Tyr Asp Gly Ile Pro Ala Ser Glu Ile Ser Ser
                755                 760                 765

Ile Leu Glu Lys Gly Glu Arg Leu Pro Gln Pro Ile Cys Thr Ile
                770                 775                 780

Asp Val Tyr Met Ile Met Val Lys Cys Trp Met Ile Asp Ala Asp Ser
785                 790                 795                 800

Arg Pro Lys Phe Arg Glu Leu Ile Ile Glu Phe Ser Lys Met Ala Arg
                805                 810                 815

Asp Pro Gln Arg Tyr Leu Val Ile Gln Gly Asp Glu Arg Met His Leu
                820                 825                 830

Pro Ser Pro Thr Asp Ser Asn Phe Tyr Arg Ala Leu Met Asp Glu Glu
                835                 840                 845

Asp Met Asp Asp Val Val Asp Ala Asp Glu Tyr Leu Ile Pro Gln Gln
850                 855                 860

Gly Phe Phe Ser Ser Pro Ser Thr Ser Arg Thr Pro Leu Leu Ser Ser
865                 870                 875                 880

Leu Ser Ala Thr Ser Asn Asn Ser Thr Val Ala Cys Ile Asp Arg Asn
                885                 890                 895

Gly Leu Gln Ser Cys Pro Ile Lys Glu Asp Ser Phe Leu Gln Arg Tyr
                900                 905                 910

Ser Ser Asp Pro Thr Gly Ala Leu Thr Glu Asp Ser Ile Asp Asp Thr
                915                 920                 925

Phe Leu Pro Val Pro Glu Tyr Ile Asn Gln Ser Val Pro Lys Arg Pro
                930                 935                 940

Ala Gly Ser Val Gln Asn Pro Val Tyr His Asn Gln Pro Leu Asn Pro
945                 950                 955                 960

Ala Pro Ser Arg Asp Pro His Tyr Gln Asp Pro His Ser Thr Ala Val
                965                 970                 975

Gly Asn Pro Glu Tyr Leu Asn Thr Val Gln Pro Thr Cys Val Asn Ser
                980                 985                 990

Thr Phe Asp Ser Pro Ala His Trp Ala Gln Lys Gly Ser His Gln Ile
                995                 1000                1005

Ser Leu Asp Asn Pro Asp Tyr Gln Gln Asp Phe Phe Pro Lys Glu
                1010                1015                1020
```

```
Ala Lys Pro Asn Gly Ile Phe Lys Gly Ser Thr Ala Glu Asn Ala
    1025                1030                1035

Glu Tyr Leu Arg Val Ala Pro Gln Ser Ser Glu Phe Ile Gly Ala
    1040                1045                1050

<210> SEQ ID NO 3
<211> LENGTH: 990
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Phe Val
65                  70                  75                  80

Val Thr Asp His Gly Ser Cys Val Arg Ala Cys Gly Ala Asp Ser Tyr
                85                  90                  95

Glu Met Glu Glu Asp Gly Val Arg Lys Cys Lys Cys Glu Gly Pro
            100                 105                 110

Cys Arg Lys Val Cys Asn Gly Ile Gly Ile Gly Glu Phe Lys Asp Ser
        115                 120                 125

Leu Ser Ile Asn Ala Thr Asn Ile Lys His Phe Lys Asn Cys Thr Ser
    130                 135                 140

Ile Ser Gly Asp Leu His Ile Leu Pro Val Ala Phe Arg Gly Asp Ser
145                 150                 155                 160

Phe Thr His Thr Pro Pro Leu Asp Pro Gln Glu Leu Asp Ile Leu Lys
                165                 170                 175

Thr Val Lys Glu Ile Thr Gly Phe Leu Leu Ile Gln Ala Trp Pro Glu
            180                 185                 190

Asn Arg Thr Asp Leu His Ala Phe Glu Asn Leu Glu Ile Ile Arg Gly
        195                 200                 205

Arg Thr Lys Gln His Gly Gln Phe Ser Leu Ala Val Val Ser Leu Asn
    210                 215                 220

Ile Thr Ser Leu Gly Leu Arg Ser Leu Lys Glu Ile Ser Asp Gly Asp
225                 230                 235                 240

Val Ile Ile Ser Gly Asn Lys Asn Leu Cys Tyr Ala Asn Thr Ile Asn
                245                 250                 255

Trp Lys Lys Leu Phe Gly Thr Ser Gly Gln Lys Thr Lys Ile Ile Ser
            260                 265                 270

Asn Arg Gly Glu Asn Ser Cys Lys Ala Thr Gly Gln Val Cys His Ala
        275                 280                 285

Leu Cys Ser Pro Glu Gly Cys Trp Gly Pro Glu Pro Arg Asp Cys Val
    290                 295                 300

Ser Cys Arg Asn Val Ser Arg Gly Arg Glu Cys Val Asp Lys Cys Asn
305                 310                 315                 320

Leu Leu Glu Gly Glu Pro Arg Glu Phe Val Glu Asn Ser Glu Cys Ile
```

```
                    325                 330                 335
        Gln Cys His Pro Glu Cys Leu Pro Gln Ala Met Asn Ile Thr Cys Thr
                        340                 345                 350
        Gly Arg Gly Pro Asp Asn Cys Ile Gln Cys Ala His Tyr Ile Asp Gly
                        355                 360                 365
        Pro His Cys Val Lys Thr Cys Pro Ala Gly Val Met Gly Glu Asn Asn
                        370                 375                 380
        Thr Leu Val Trp Lys Tyr Ala Asp Ala Gly His Val Cys His Leu Cys
        385                 390                 395                 400
        His Pro Asn Cys Thr Tyr Gly Cys Thr Gly Pro Gly Leu Glu Gly Cys
                        405                 410                 415
        Pro Thr Asn Gly Pro Lys Ile Pro Ser Ile Ala Thr Gly Met Val Gly
                        420                 425                 430
        Ala Leu Leu Leu Leu Leu Val Val Ala Leu Gly Ile Gly Leu Phe Met
                        435                 440                 445
        Arg Arg Arg His Ile Val Arg Lys Arg Thr Leu Arg Arg Leu Leu Gln
                        450                 455                 460
        Glu Arg Glu Leu Val Glu Pro Leu Thr Pro Ser Gly Glu Ala Pro Asn
        465                 470                 475                 480
        Gln Ala Leu Leu Arg Ile Leu Lys Glu Thr Glu Phe Lys Lys Ile Lys
                        485                 490                 495
        Val Leu Gly Ser Gly Ala Phe Gly Thr Val Tyr Lys Gly Leu Trp Ile
                        500                 505                 510
        Pro Glu Gly Glu Lys Val Lys Ile Pro Val Ala Ile Lys Glu Leu Arg
                        515                 520                 525
        Glu Ala Thr Ser Pro Lys Ala Asn Lys Glu Ile Leu Asp Glu Ala Tyr
                        530                 535                 540
        Val Met Ala Ser Val Asp Asn Pro His Val Cys Arg Leu Leu Gly Ile
        545                 550                 555                 560
        Cys Leu Thr Ser Thr Val Gln Leu Ile Thr Gln Leu Met Pro Phe Gly
                        565                 570                 575
        Cys Leu Leu Asp Tyr Val Arg Glu His Lys Asp Asn Ile Gly Ser Gln
                        580                 585                 590
        Tyr Leu Leu Asn Trp Cys Val Gln Ile Ala Lys Gly Met Asn Tyr Leu
                        595                 600                 605
        Glu Asp Arg Arg Leu Val His Arg Asp Leu Ala Ala Arg Asn Val Leu
                        610                 615                 620
        Val Lys Thr Pro Gln His Val Lys Ile Thr Asp Phe Gly Leu Ala Lys
        625                 630                 635                 640
        Leu Leu Gly Ala Glu Glu Lys Glu Tyr His Ala Glu Gly Gly Lys Val
                        645                 650                 655
        Pro Ile Lys Trp Met Ala Leu Glu Ser Ile Leu His Arg Ile Tyr Thr
                        660                 665                 670
        His Gln Ser Asp Val Trp Ser Tyr Gly Val Thr Val Trp Glu Leu Met
                        675                 680                 685
        Thr Phe Gly Ser Lys Pro Tyr Asp Gly Ile Pro Ala Ser Glu Ile Ser
                        690                 695                 700
        Ser Ile Leu Glu Lys Gly Glu Arg Leu Pro Gln Pro Pro Ile Cys Thr
        705                 710                 715                 720
        Ile Asp Val Tyr Met Ile Met Val Lys Cys Trp Met Ile Asp Ala Asp
                        725                 730                 735
        Ser Arg Pro Lys Phe Arg Glu Leu Ile Ile Glu Phe Ser Lys Met Ala
                        740                 745                 750
```

Arg Asp Pro Gln Arg Tyr Leu Val Ile Gln Gly Asp Glu Arg Met His
                755                 760                 765

Leu Pro Ser Pro Thr Asp Ser Asn Phe Tyr Arg Ala Leu Met Asp Glu
    770                 775                 780

Glu Asp Met Asp Val Val Asp Ala Asp Glu Tyr Leu Ile Pro Gln
785                 790                 795                 800

Gln Gly Phe Phe Ser Ser Pro Ser Thr Ser Arg Thr Pro Leu Leu Ser
                805                 810                 815

Ser Leu Ser Ala Thr Ser Asn Asn Ser Thr Val Ala Cys Ile Asp Arg
            820                 825                 830

Asn Gly Leu Gln Ser Cys Pro Ile Lys Glu Asp Ser Phe Leu Gln Arg
        835                 840                 845

Tyr Ser Ser Asp Pro Thr Gly Ala Leu Thr Glu Asp Ser Ile Asp Asp
850                 855                 860

Thr Phe Leu Pro Val Pro Glu Tyr Ile Asn Gln Ser Val Pro Lys Arg
865                 870                 875                 880

Pro Ala Gly Ser Val Gln Asn Pro Val Tyr His Asn Gln Pro Leu Asn
                885                 890                 895

Pro Ala Pro Ser Arg Asp Pro His Tyr Gln Asp Pro His Ser Thr Ala
            900                 905                 910

Val Gly Asn Pro Glu Tyr Leu Asn Thr Val Gln Pro Thr Cys Val Asn
        915                 920                 925

Ser Thr Phe Asp Ser Pro Ala His Trp Ala Gln Lys Gly Ser His Gln
    930                 935                 940

Ile Ser Leu Asp Asn Pro Asp Tyr Gln Gln Asp Phe Phe Pro Lys Glu
945                 950                 955                 960

Ala Lys Pro Asn Gly Ile Phe Lys Gly Ser Thr Ala Glu Asn Ala Glu
                965                 970                 975

Tyr Leu Arg Val Ala Pro Gln Ser Ser Glu Phe Ile Gly Ala
            980                 985                 990

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttgccaaggc acctgcgtga a                                              21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggcgagtcgg gctctggagg aaaag                                          25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic -continued

```
                primer

<400> SEQUENCE: 6
ggcccttcgc acttcttaca cttg                                           24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cctggggatc ggcctcttca t                                              21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caccccgtag ctccagacat ca                                             22

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Cys Gln Gly Thr Cys Val Lys Lys Cys Pro
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Lys Lys Gly Gln Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Ser Phe Phe Val Val Thr
1               5

<210> SEQ ID NO 12
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 12

Gly Gly Gly Gly Ser Gly Gly Gly Gly Ser Gly Gly Gly Gly Ser
1               5                   10                  15

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tgccaaggca cctgcgtg                                                   18

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gaaaagaaag gtaattatgt g                                               21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaaaagaaag gccaaaagt                                                  19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctttccttct ttgtggtgac a                                               21

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17 atcycagaag                                                            10

<210> SEQ ID NO 18
<211> LENGTH: 10
<212> TYPE: DNA
<213> ORGANISM: Unknown
```

```
<220> FEATURE:
<223> OTHER INFORMATION: Description of Unknown: Wild type HNSCC
      oligonucleotide

<400> SEQUENCE: 18
atcccagaag                                                              10

<210> SEQ ID NO 19
<211> LENGTH: 1006
<212> TYPE: DNA
<213> ORGANISM: Homo sapiens

<400> SEQUENCE: 19
atgcgaccct ccgggacggc cggggcagcg ctcctggcgc tgctggctgc gctctgcccg        60
gcgagtcggg ctctggagga aaagaaagtt tgccaaggca cgagtaacaa gctcacgcag       120
ttgggcactt ttgaagatca tttctcagc ctccagagga tgttcaataa ctgtgaggtg        180
gtccttggga atttggaaat tacctatgtg cagaggaatt atgatctttc cttcttaaag       240
accatccagg aggtggctgg ttatgtcctc attgccctca acacagtgga gcgaattcct       300
ttggaaaacc tgcagatcat cagaggaaat atgtactacg aaaattccta tgccttagca      360
gtcttatcta actatgatgc aaataaaacc ggactgaagg agctgcccat gagaaattta       420
caggaaatcc tgcatggcgc cgtgcggttc agcaacaacc ctgccctgtg caacgtggag       480
agcatccagt ggcgggacat agtcagcagt gactttctca gcaacatgtc gatggacttc       540
cagaaccacc tgggcagctg ccaaaagtgt gatccaagct gtcccaatgg gagctgctgg       600
ggtgcaggag aggagaactg ccagaaactg accaaaatca tctgtgccca gcagtgctcc       660
gggcgctgcc gtggcaagtc ccccagtgac tgctgccaca accagtgtgc tgcaggctgc       720
acaggccccc gggagagcga ctgcctggtc tgccgcaaat ccgagacga agccacgtgc       780 aaggacacct gcccccact catgctctac aaccccacca cgtaccagat ggatgtgaac       840
cccgagggca aatacagctt tggtgccacc tgcgtgaaga gtgtccccg taattatgtg        900 gtgacagatc acggctcgtg cgtccgagcc tgtggggccg acagctatga gatggaggaa      960
gacggcgtcc gcaagtgtaa gaagtgcgaa gggccttgcc gcaaag                     1006

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aagaaaggta attatg                                                       16
```